United States Patent
Ford et al.

(10) Patent No.: US 7,456,187 B2
(45) Date of Patent: Nov. 25, 2008

(54) FURANOPYRIMIDINE COMPOUNDS AS POTASSIUM ION CHANNEL INHIBITORS

(75) Inventors: John Ford, Huntingdon (GB); Nicholas John Palmer, Cambridge (GB); John Frederick Atherall, Essex (GB); David John Madge, West Sussex (GB)

(73) Assignee: Xention Limited, Pampisford, Cambridge (GB)

( * ) Notice: Subject to any disclaimer, the term of this patent is extended or adjusted under 35 U.S.C. 154(b) by 279 days.

(21) Appl. No.: 11/148,991

(22) Filed: Jun. 10, 2005

(65) Prior Publication Data
US 2005/0282829 A1 Dec. 22, 2005

Related U.S. Application Data

(60) Provisional application No. 60/578,350, filed on Jun. 10, 2004.

(30) Foreign Application Priority Data
Jun. 10, 2004 (GB) .................................. 0412986.2

(51) Int. Cl.
C07D 491/048 (2006.01)
A61K 31/519 (2006.01)
A61P 9/06 (2006.01)
(52) U.S. Cl. ..................................... 514/260.1; 544/278
(58) Field of Classification Search ................. 544/278; 514/260.1
See application file for complete search history.

(56) References Cited

U.S. PATENT DOCUMENTS

| | | | | |
|---|---|---|---|---|
| 4,199,584 | A | * | 4/1980 | Cox et al. ................. 514/260.1 |
| 5,137,879 | A | * | 8/1992 | Edie et al. ....................... 514/63 |
| 6,531,495 | B1 | | 3/2003 | Brendel et al. |
| 2002/0161011 | A1 | | 10/2002 | Beaudoin et al. |
| 2003/0027829 | A1 | | 2/2003 | Reed et al. |
| 2005/0026935 | A1 | | 2/2005 | Ford et al. |
| 2006/0183768 | A1 | | 8/2006 | Ford et al. |
| 2007/0161672 | A1 | | 7/2007 | Ford et al. |

FOREIGN PATENT DOCUMENTS

| | | |
|---|---|---|
| AU | 521790 | 11/1979 |
| DE | 226 893 A1 | 9/1985 |
| DE | 101 04 802 A1 | 8/2002 |
| GB | 1 570 494 | 7/1980 |
| JP | 48-81892 | 11/1973 |
| JP | 48-81893 | 11/1973 |
| RU | 2 116 309 C1 | 7/1998 |
| WO | WO 98/04521 A1 | 2/1998 |
| WO | WO 98/04542 A1 | 2/1998 |
| WO | WO 98/18475 A1 | 5/1998 |
| WO | WO 98/18476 A1 | 5/1998 |
| WO | WOX 99/37607 A1 | 7/1999 |
| WO | WO 99/62891 A1 | 12/1999 |
| WO | WO 00/12492 A1 | 3/2000 |
| WO | WO 00/25774 A1 | 5/2000 |
| WO | WO 01/00573 A1 | 1/2001 |
| WO | WO 01/21609 A1 | 3/2001 |
| WO | WO 01/21610 A1 | 3/2001 |
| WO | WO 01/25189 A1 | 4/2001 |
| WO | WO 01/25224 A1 | 4/2001 |
| WO | WO 01/40231 A1 | 6/2001 |
| WO | WO 01/46155 A1 | 6/2001 |
| WO | WO 02/24655 A1 | 3/2002 |
| WO | WO 01/27107 A2 | 4/2002 |
| WO | WO 02/36556 A2 | 5/2002 |
| WO | WO 02/44137 A1 | 6/2002 |
| WO | WO 02/46162 A1 | 6/2002 |
| WO | WO 02/48131 A1 | 6/2002 |
| WO | WO 02/064581 A1 | 8/2002 |
| WO | WO 02/087568 A1 | 11/2002 |
| WO | WO 02/088073 A1 | 11/2002 |
| WO | WO 02/100825 A2 | 12/2002 |
| WO | WO 03/000675 A1 | 1/2003 |
| WO | WO 03/063797 A2 | 8/2003 |

OTHER PUBLICATIONS

Hackler et. al. (Special Publication—Royal Society of Chemistry., 1994, 147, 70-84). CAS print out 44/74.*

(Continued)

Primary Examiner—Brenda L. Coleman
Assistant Examiner—Susanna Moore
(74) Attorney, Agent, or Firm—Sterne, Kessler, Goldstein & Fox P.L.L.C.

(57) ABSTRACT

A compound of formula (I)

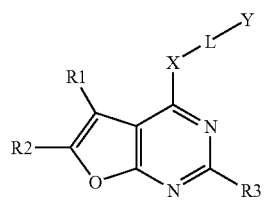

wherein
$R_1$ is aryl, heteroaryl, cycloalkyl or alkyl;
$R_2$ is H, alkyl, nitro, —$CO_2R_7$, $CONR_4R_5$ or halo;
$R_3$ is H, $NR_4R_5$, $NC(O)R_8$, halo, trifluoromethyl, alkyl, nitrile or alkoxy;
$R_4$ and $R_5$ may be the same or different, and may be H, alkyl, aryl, heteroaryl or cycloalkyl; or $R_4$ and $R_5$ may together form a saturated, unsaturated or partially saturated 4 to 7 member ring, wherein said ring may optionally comprise one or more further heteroatoms selected from N, O or S;
X is O, S or $NR_6$;
$R_6$ is H or alkyl;
$R_7$ is hydrogen, methyl or ethyl;
$R_8$ is methyl or ethyl;
L is $(CH_2)_n$, where n is 1, 2 or 3; and
Y is aryl, a heterocyclic group, alkyl, alkenyl or cycloalkyl;
together with pharmaceutically acceptable salts thereof. The use of these compounds as potassium channel inhibitors is also described.

20 Claims, No Drawings

OTHER PUBLICATIONS

Belenkii et. al. (Khimiya Geterotsiklicheskikh, 1993, 1, 124-129) CAS printount 46/74.*

Amos, G.J., et al., "Differences between outward currents of human atrial and subepicardial ventricular myocytes," *J. Physiol. 491*:31-50, Cambridge Univ. Press. (1996).

Armstrong, C.M. and Hille, B., "Voltage-Gated Ion Channels and Electrical Excitability," *Neuron 20*:371-380, Cell Press (1998).

Bachmann, A., et al., "Characterization of a novel Kv1.5 channel blocker in *Xenopus* oocytes, CHO cells, human and rat cardiomyocytes," *Naunyn-Schmiedeberg's Arch. Pharmacol. 364*:472-478, Springer-Verlag (2001).

Belen'kii, L.I., et al., "Synthesis of Heterocyclic Compounds from the Products of Addition of Polyhaloalkanes to Unsaturated Systems. 4. Synthesis of Substituted Furo[2,3-D]Pyrimidines," *Chemistry of Heterocyclic Compounds 29*:109-114, Plenum Publishing Corporation (1993).

Brendel, J. and Peukert, S., "Blockers of the Kv1.5 channel for the treatment of atrial arrhythmias," *Expert Opin. Ther. Patents 12*:1589-1598, Ashley Publications Ltd. (2002).

Campaigne, E., "Thiophenes and their Benzo Derivatives: (iii) Synthesis and Applications," in *Comprehensive Heterocyclic Chemistry: The Structure, Reactions, Synthesis and Uses of Heterocyclic Compounds 4*, Bird, C.W., et al., eds., Pergamon Press, New York, NY, pp. 863-934 (1984).

Colatsky, T.J., et al., "Channel Specificity in Antiarrhythmic Drug Action: Mechanism of Potassium Channel Block and Its Role in Suppressing and Aggravating Cardiac Arrhythmias," *Circulation 82*:2235-2242, American Heart Association (1990).

Courtemanche, M.,, et al., "Ionic targets for drug therapy and atrial fibrillation-induced electrical remodeling: insights from a mathematical model," *Cardiovasc. Res. 42*:477-489, Elsevier Science B. V. (1999).

Fedida, D., et al., "Identity of a Novel Delayed Rectifier Current From Human Heart With a Cloned $K^+$ Channel Current," *Circ. Res. 73*:210-216, Lippincott Williams & Wilkins (1993).

Feng, J., et al., "Antisense Oligodeoxynucleotides Directed Against Kv1.5 mRNA Specifically Inhibit Ultrarapid Delayed Rectifier $K^+$ Current in Cultured Adult Human Atrial Myocytes," *Cir. Res. 80*:572-579, American Heart Association, Inc. (1997).

Feng, J., et al., "Effects of Class III Antiarrhythmic Drugs on Transient Outward and Ultra-rapid Delayed Rectifier Currents in Human Atrial Myocytes," *J. Pharmacol. Exp. Ther. 281*:384-392, American Society for Pharmacology and Experimental Therapeutics (1997).

Ford, J. W., et al., "Potassium Channels: Gene Family, Therapeutic Relevance, High-Throughput Screening Technologies and Drug Discovery," in *Progress in Drug Research, vol. 58*, Jucker, E., ed., Birkhäuser Verlag, Boston, MA, pp. 133-168 (2002).

Godreau, D., et al., "Mechanisms of Action of Antiarrythmic Agent Bertosamil on hKv1.5 Channels and Outward Potassium Current in Human Atrial Myocytes," *J. Pharmacol. Exp. Ther. 300*:612-620, American Society for Pharmacology and Experimental Therapeutics (2002).

Gutman, G.A., et al., "International Union of Pharmacology. XLI. Compendium of Voltage-Gated Ion Channels: Potassium Channels," *Pharmacol. Rev. 55*:583-586, American Society for Pharmacology and Experimental Therapeutics (Dec. 2003).

Herbert, S.C., "General Principles of the Structure of Ion Channels," *Am. J. Med. 104*:87-98, Excerpta Medica, Inc. (1998).

Hosni, H.M., et al., "Thienopyrimidines II: Synthesis of Newer Thieno[2,3-d]-Pyrimidines and Their Quaternized Derivatives with Molluscicidal Activity," *Acta Pol. Pharm.—Drug Res. 56*:49-56, Polish Pharmaceutical Society (1999).

Hozien, Z.A., et al., "Synthesis and Application of Some New Thienopyrimidine Dervatives as Antimicrobial Agents," *Synthetic Communications 26*:3733-3755, Marcel Dekker, Inc. (1996).

Ismail, K.A., et al., "Synthesis and Antimicrobial Activity of Some Tetramethylenethieno[2,3-d]pyrimidine derivatives," *Il Farmaco 50*:611-616, Elsevier (1995).

Jordis, U., et al., "7,9-Dideaza-9-Thiaadenines (4-Aminothieno/2,3-d/pyrimidines) as Potential Anticytokinines," *Vestn. Slov. Kem. Drus. 33*:217-238, Drustvo (1986).

Katada, J., et al., "Cytotoxic effects of NSL-1406, a new thienopyrimidine derivative, on leukocytes and osteoclasts," *Bioorg. Med. Chem. Lett. 9*:797-802, Elsevier Science Ltd. (1999).

Knobloch, K., et al., "Electrophysiological and antiarrhythmic effects of the novel $I_{Kur}$ channel blockers, S9947 and S20951, on left vs. right pig atrium in vivo in comparison with the $I_{Kr}$ blockers dofetilide, azimilide, d,l-sotalol and ibutilide," *Naunyn-Schmiedeberg's Arch. Pharmacol. 366*:482-487, Springer-Verlag (2002).

Konno, S., et al., "Synthesis of Thienopyrimidine Derivatives and Their Antifungal Activities," *Yakugaku Zasshi 109*:464-473, Pharmaceutical Society of Japan (1989).

Li, G.-R., et al., "Evidence for Two Components of Delayed Rectifier $K^+$ Current in Human Ventricular Myocytes," *Circ. Res. 78*:689-696, American Heart Association, Inc. (1996).

Malayev, A.A., et al., "Mechanism of Clofilium Block of the Human Kv1.5 Delayed Rectifier Potassium Channel," *Mol. Pharmacol. 47*:198-205, American Society for Pharmacology and Experimental Therapeutics (1995).

Marbán, E., "Cardiac channelopathies," *Nature 415*:213-218, Macmillian Magazines Ltd. (2002).

Matsuda, T., et al., "Inhibition by a novel anti-arrhythmic agent, NIP-142, of cloned human cardiac $K^+$ channel Kv1.5 current," *Life Sci. 68*:2017-2024, Elsevier Science, Inc. (2001).

Moneer, A.A., et al., "Reaction of 3-Amino and 4-hydrazino-5,6-Tetramethylenethieno[2,3-d]Pyrimidine Derivatives with Azlactones," *Egypt. J. Pharm. Sci. 34*:599-609, National Information & Documentation Centre (1993).

Munchhof, M.J., et al., "Design and SAR of thienopyrimidine and thienopyridine inhibitors of VEGFR-2 kinase activity," *Bioorg. Med. Chem. Lett. 14*:21-24, Elsevier Ltd. (Jan. 2004).

Nakayama, J., "Thiophenes and their Benzo Derivatives: Synthesis," in *Comprehensive Heterocyclic Chemistry II, vol. 2*: Katritzky, A.R., et al., eds., pp. 607-677, Pergamon Press, New York, NY (1996).

Nattel, S., et al., "Cardiac Ultrarapid Delayed Rectifiers: A Novel Potassium Current Family of Functional Similarity and Molecular Diversity," *Cell Physiol. Biochem. 9*:217-226, S. Karger AG (1999).

Nattel, S., "Therapeutic implications of atrial fibrillation mechanisms: can mechanistic insights be used to improve AF management?," *Cardiovasc. Res. 54*:347-360, Elsevier Science B.V. (2002).

Noravyan, A.S., et al., "Synthesis and anticonvulsive activity of 4-alkyl (or aryl)amino-6,6-dimethyl-5,6-dihydro-8H-pyrano (or thiopyrano)[3,4-b]thieno[5,4-d] pyrimidines," *Khimiko-Farmatsevticheskii Zhurnal 11*:38-42, Folium Publishing Company (1977).

Peukert, S., et al., "Identification, Synthesis, and Activity of Novel Blockers of the Voltage-Gated Potassium Channel Kv1.5," *J. Med. Chem. 46*:486-498, American Chemical Society (Feb. 2003).

Ram, V.J., "Thieno[2,3-*d*]pyrimidines as Potential Chemotherapeutic Agents," *Arch. Pharm. (Weinheim) 312*:19-25, Verlag Chemie, GmbH (1979).

Ram, V.J., et al., "Thieno[2,3-*d*]pyrimidines as Potential Chemotherapeutic Agents. II," *J. Heterocylic Chem. 18*:1277-1280, HeteroCorporation (1981).

Shehata, I.A., et al., "Synthesis, Antitumor and Anti-HIV-1 Testing of Certain Thieno[2,3-*d*]pyrimidine, Thieno[2,3-*d*]imidazo[1,2-c]pyrimidine and Thieno[2,3-*d*][1,3]thiazine Derivatives," *Med. Chem. Res. 6*:148-163, Birkhäuser Boston (1996).

Shieh, C.-C., et al., "Potassium Channels: Molecular Defects, Diseases, and Therapeutic Opportunities," *Pharmacol. Rev. 52*:557-593, American Society for Pharmacology and Experimental Therapeutics (2000).

Stewart, A.O., et al., "Discovery of Inhibitors of Cell Adhesion Molecule Expression in Human Endothelial Cells. 1. Selective Inhibition of ICAM-1 and E-Selectin Expression," *J. Med. Chem. 44*:988-1002, American Chemical Society (2001).

Tyle, P., "Iontophoretic Devices for Drug Delivery," *Pharm. Res. 3*:318-326, Plenum Publishing Corporation (1986).

Wang, Z., et al., "Sustained Depolarization-Induced Outward Current in Human Atrial Myocytes: Evidence for a Novel Delayed Rectifier K⁺ Current Similar to Kv1.5 Cloned Channel Currents," *Circ. Res.* 73:1061-1076, American Heart Association (1993).

Wang, Z., et al., "Effects of Flecainide, Quinidine, and 4-Aminopyridine on Transient Outward and Ultrarapid Delayed Rectifier Currents in Human Atrial Myocytes," *J. Pharmacol. Exp. Ther.* 272:184-196 (1995).

Wirth, K.J., et al., "Atrial effects of the novel K⁺-channel-blockers AVE0118 in anesthetized pigs," *Cardiovasc. Res.* 60:298-306, Elsevier B.V. (Nov. 2003).

Xu, D.H. and Xu, S.B., "The Expression of Arrhythmic Related Genes on *Xenopus* Oocytes for Evaluation of Class III Antiarrhythmic Drugs from Ocean Active Material," *Acta Genetica Sinica* 27:195-201, Science Press and Elsevier Press (2000).

Dialog File 351, Acession No. 607591, Derwent WPI English language abstract for JP 48-81892 (listed on accompanying PTO/SB/08A as document FP1), downloaded Mar. 14, 2007.

Dialog File 351, Accession No. 607592, Derwent WPI English language abstract for JP 48-81893 (listed on accompanying PTO/SB/08A as document FP2), downloaded Mar. 14, 2007.

Dialog File 351, Accession No. 3566123, Derwent WPI English language abstract for DD 226 893 A1 (listed on accompanying PTO/SB/08A as document FP10), downloaded Mar. 14, 2007.

Dialog File 351, Accession No. 12964595, Derwent WPI English language abstract for DE 101 04 802 A1 (listed on accompanying PTO/SB/08A as document FP23), downloaded Mar. 2007.

Co-pending U.S. Appl. No. 11/635,786, inventors Ford, J., et al., filed Dec. 8, 2006.

STNEasy Database, Accession No. 1978:37739, English language abstract for Noravyan, A.S., et al., "Synthesis and anticonvulsive activity of 4-alkyl (or aryl)amino-6,6-dimethyl-5,6-dihydro-8H-pyrano (or thiopyrano)[3,4-b]thieno[5,4-d] pyrimidines," *Khimiko-Farmatsevticheskii Zhurnal* 11:38-42, Folium Publishing Company (1977).

Abdelrazek, F.M., et al., "Synthesis of Novel Thieno[2,3-d]pyrimidine, Thieno[2,3-b]pyridine and Thiazolo[3,2-a]thieno[2,3-d]pyrimidine Derivatives and their effect on the production of Mycotoxines," *Arch. Pharm. (Weinheim)* 325:301-306, VCH Verlagsgesellschaft mbH (1992).

Baell, J.B., et al., "Khellinone Derivatives as Blockers of the Voltage-Gated Potassium Channel Kv1.3: Synthesis and Immunosuppressive Activity," *J. Med. Chem.* 47:2326-2336, American Chemical Society (Apr. 2004).

Barker, J.M., et al., "Thienopyridines. Part 6. Synthesis and Nucleophilic Substitution of Some Chlorothieno[2,3-b]pyridine Derivatives, and Comparisons with the Analogous Quinoline Compounds," *J. Chem. Research (M)*:2501-2523, Science Reviews, Ltd. (1985).

Beeton, C., et al., "Selective blockade of T lymphocyte K⁺ channels ameliorates experimental autoimmune encephalomyelitis, a model for multiple sclerosis," *Proc. Natl. Acad. Sci. USA* 98:13942-13947, National Academy of Sciences (2001).

Beeton, C., et al., "A Novel Fluorescent Toxin to Detect and Investigate Kv1.3 Channel Up-regulation in Chronically Activated T Lymphocytes," *J. Biol. Chem.* 278:9928-9937, American Society for Biochemistry and Molecular Biology, Inc. (Mar. 2003).

Boschelli, D.H., et al., "Identification of 7-Phenylaminathieno-[3,2-b]pyridine-6-carbonitriles as a New Class of Src Kinase Inhibitors," *J. Med. Chem.* 47:6666-6668, American Chemical Society (Dec. 2004).

Charvát, T., et al., "Diethyl Acetonedicarboxylate—a Precursor for the Synthesis of New Substituted 4-Aminoquinolines and Fused 4-Aminopyridines," *Monatshefte für Chemie* 126:333-340, Springer-Verlag (1995).

Desir, G.V., "Kv1.3 potassium channel blockade as an approach to insulin resistance," *Expert Opin. Ther. Targets* 9:571-579, Ashley Publications Ltd. (Jun. 2005).

Felix, J.P., et al., "Identification and Biochemical Characterization of a Novel Nortriterpene Inhibitor of the Human Lymphocyte Voltage-Gated Potassium Channel, Kv1.3," *Biochemistry* 38:4922-4930, American Chemical Society (1999).

Friedrich, M., et al., "Flow cytometric characterization of lesional T cells in psoriasis: intracellular cytokine and surface antigen expression indicates an activated, memory/effector type 1 immunophenotype," *Arch. Dermatol. Res.* 292:519-521, Springer-Verlag (2000).

Gewald, K., et al., "Synthesen von 4-Amino-thieno[2,3-b]pyridinen," *Monatshefte füChemie* 110:1189-1196, Springer-Verlag (1979).

Gilis, P.M., et al., "Synthesis and antibacterial evaluation of 4,7-dihydro-4-oxothieno[2,3-b] pyridine-5-carboxylic acids," *Eur. J. Med. Chem. Chim. Ther.* 13:265-269, Editions Scientifiques Elsevier (1978).

Hanson, D.C., et al., "UK-78,282, a novel piperidine compounds that potently blocks the Kv1.3 voltage-gated potassium channel and inhibits human T cell activation," *Br. J. Pahrmacol.* 126:1707-1716, Stockton Press (1999).

Leonard, R.J., et al., "Selective blockers of voltage gated K⁺ channels depolarize human T lymphocytes: Mechanism of the antiproliferative effect of charybdotoxin," *Proc. Natl. Acad. Sci. USA* 89:10094-10098, National Academy of Sciences (1992).

Marco, J.L., et al., "Synthesis and Acetylcholinesterase/Butyrylcholinesterase Inhibition Activity of 4-Amino-2,3-diaryl-5,6,7,8-tetrahydrofuro(and thieno)[2,3-b]-quinolines, and 4-Amino-5,6,7,8,9-pentahydro-2,3-diphenylcyclohepta[e]furo(and thieno)-[2,3-b]pyridines," *Arch. Pharm. Pharm. Med. Chem.* 335:347-353, Wiley-VCH GmbH & Co. (2002).

Meadows, H.J., et al., "Effect of SB-205384 on the decay of GABA-activated chloride currents in granule cells cultured from rat cerebellum," *Br. J. Pharmacol.* 121:1334-1338, Stockton Press (1997).

Nguyen, A., et al., "Novel Nonpeptide Agents Potently Block the C-Type Inactivated Conformation of Kv1.3 and Suppress T Cell Activation," *Mol. Pharmacol.* 50:1672-1679, American Society for Pharmacology and Experimental Therapeutics (1996).

O'Connor, K.C., et al., "The Neuroimmunology of Multiple Sclerosis: Possible Roles of T and B Lymphocytes in Immunopathogenesis," *J. Clin. Immunol.* 21:81-92, Plenum Publishing Corporation (2001).

Page, R.L. and Roden, D.M., "Drug Therapy for Atrial Fibrillation: Where Do We Go from Here?," *Nat. Rev. Drug Discov.* 4:899-910, Nature Publishing Group (Nov. 2005).

Schmitz, A., et al., "Design of PAP-1, a Selective Small Molecule Kv1.3 Blocker, for the Suppression of Effector Memory T Cells in Autoimmune Diseases," *Mol. Pharmacol.* 68:1254-1270, American Society for Pharmacology and Experimental Therapeutics (Nov. 2005).

Shah, K., et al., "Immunosuppressive effects of a Kv1.3 inhibitor," *Cell. Immunol.* 221:100-106, Elsevier Science (Feb. 2003).

Suzuki, M., et al., "Synthesis and Biological Evaluations of Condensed Pyridine and Condensed Pyrimidine-Based HMG-CoA Reductase Inhibitors," *Bioorg. Med. Chem. Lett.* 11:1285-1288, Elsevier Science Ltd (2001).

Valverde, P., et al., "Potassium Channel-blockers as Therapeutic Agents to Interfere with Bone Resorption Disease," *J. Dent. Res.* 84:488-499, International & American Associations for Dental Research (Jun. 2005).

Vennekamp, J., et al., "Kv1.3-Blocking 5-Phenylalkoxypsoralens: A New Class for Immunomodulators," *Mol. Pharmacol.* 65:1364-1374, American Society for Pharmacology and Experimental Therapeutics (Jun. 2004).

Viglietta, V., et al., "GAD65-reactive T cells are activated in patients with autoimmune type 1a diabetes," *J. Clin. Invest.* 109:895-903, American Society for Clinical Investigation (2002).

Wulff, H., et al., "Alkoxypsoralens, Novel Nonpeptide Blockers of *Shaker*-Type K⁺ Channels: Synthesis and Photoreactivity," *J. Med. Chem.* 41:4542-4549, American Chemical Society (1998).

Wulff, H., et al., "Potassium channels as therapeutic targets for autoimmune disorders," *Curr. Opin. Drug Discov. Devel.* 6:640-647, Thomson Scientific (Sep. 2003).

Wulff, H., et al., "The voltage-gated Kv1.3 k⁺ Channel in effector memory T cells as new targets for MS," *J. Clin. Invest.* 111:1703-1713, American Society for Clinical Investigation (Jun. 2003).

Wulff, H., et al., "K⁺ Channel Expression during B Cell Differentiation: Implications for Immunomodulation and Autoimmunity," *J. Immunol.* 173:776-786, American Association of Immunologists, Inc. (Jul. 2004).

Xu, J., et al., "The voltage-gated potassium channel Kv1.3 regulates peripheral insulin sensitivity," *Proc. Natl. Acad. Sci. USA 101*:3112-3117, National Academy of Sciences (Mar. 2004).

Yamashita, K., et al., "Severe chronic graft-versus host disease is characterized by a preponderance of CD4+ effector memory cells relative to central memory cells" *Blood 103*:3986-3988, American Society of Hematology (May 2004).

Yoon, J.-W. and Jun, H.-S., "Cellular and Molecular Pathogenic Mechanisms of Insulin-Dependent Diabetes Mellitus," *Ann. NY Acad. Sci. 928*:200-211, New York Academy of Sciences (2001).

International Search Report for International Application No. PCT/GB2004/002454, European Patent Office, Netherlands, mailed on Nov. 2, 2004.

* cited by examiner

FURANOPYRIMIDINE COMPOUNDS AS POTASSIUM ION CHANNEL INHIBITORS

CROSS REFERENCE TO RELATED APPLICATIONS

This application claims the benefit of U.S. Provisional Application No. 60/578,350, filed Jun. 10, 2004, the entirety of which is hereby incorporated by reference herein. This application claims priority under 35 U.S.C. § 119(a)-(d) to Great Britain Application No. GB 0412986.2, filed Jun. 10, 2004, the entirety of which is hereby incorporated by reference herein.

BACKGROUND OF THE INVENTION

Field of the Invention

The present invention relates to furanopyrimidine compounds which are potassium channel inhibitors. Pharmaceutical compositions comprising the compounds and their use in the treatment of arrythmia are also provided.

Ion channels are proteins that span the lipid bilayer of the cell membrane and provide an aqueous pathway through which specific ions such as $Na^+$, $K^+$, $Ca^{2+}$ and $Cl^-$ can pass (Herbert, 1998). Potassium channels represent the largest and most diverse sub-group of ion channels and they play a central role in regulating the membrane potential and controlling cellular excitability (Armstrong & Hille, 1998). Potassium channels have been categorized into gene families based on their amino acid sequence and their biophysical properties (for nomenclature see Gutman et al., 2003).

Compounds which modulate potassium channels have multiple therapeutic applications in several disease areas including cardiovascular, neuronal, auditory, renal, metabolic and cell proliferation (Shieh et al., 2000; Ford et al., 2002). More specifically potassium channels such as Kv4.3, Kir2.1, HERG, KVLQT1/minK, and Kv1.5 are involved in the repolarisation phase of the action potential in cardiac atrial myocytes. These potassium channel subtypes have been associated with cardiovascular diseases and disorders including long QT syndrome, hypertrophy, ventricular fibrillation, and atrial fibrillation, all of which can cause cardiac failure and fatality (Marban, 2002).

The human delayed rectifier voltage gated potassium channel subunit, Kv1.5, is exclusively expressed in atrial myocytes and is believed to offer therapeutic opportunities for the management of atrial fibrillation for several different reasons (see review of Brendel and Peukert, 2002): (i) There is evidence that Kv1.5 underlies the cardiac ultrarapid delayed rectifier ($Kv_{(ur)}$) physiological current in humans due to similar biophysical and pharmacological properties (Wang et al., 1993; and Fedida et al., 1993). This has been supported with antisense oligonucleotides to Kv1.5 which have been shown to reduce $Kv_{(ur)}$ amplitude in human atrial myocytes (Feng et al., 1997). (ii) electrophysiological recordings have demonstrated that $Kv_{(ur)}$ is selectively expressed in atrial myocytes, and therefore avoids inducing potentially fatal ventricular arrhythmia through interfering with ventricular repolarisation (Amos et al., 1996; Li et al., 1996; and Nattel, 2002). (iii) Inhibiting $Kv_{(ur)}$ in atrial fibrillation-type human atrial myocytes prolonged the action potential duration compared to normal healthy human atrial myocytes (Courtemanche et al., 1999). (iv) Prolonging the action potential duration by selectively inhibiting Kv1.5 could present safer pharmacological interventions for protecting against atrial re-entrant arrhythmias such as atrial fibrillation and atrial flutter compared to traditional class III antiarrythmics, by prolonging the atrial refractory period while leaving ventricular refractoriness unaltered (Nattel et al., 1999, Knobloch et al., 2002; and Wirth et al., 2003). Class III antiarrythmics have been widely reported as a preferred method for treating cardiac arrhythmias (Colatsky et al., 1990).

Traditional and novel class III antiarrythmic potassium channel blockers have been reported to have a mechanism of action by directly modulating Kv1.5 or $Kv_{(ur)}$. The known class III antiarrythmics ambasilide (Feng et al., 1997), quinidine (Wang et al., 1995), clofilium (Malayev et al., 1995) and bertosamil (Godreau et al., 2002) have all been reported as potassium channel blockers of $Kv_{(ur)}$ in human atrial myocytes. The novel benzopyran derivative, NIP-142, blocks Kv1.5 channels, prolongs the atrial refractory period and terminates atrial fibrillation and flutter in in vivo canine models (Matsuda et al., 2001), and S9947 inhibited Kv1.5 stably expressed in both Xenopus oocytes and Chinese hamster ovary (CHO) cells and $KV_{(ur)}$ in native rat and human cardiac myocytes (Bachmann et al., 2001). Elsewhere, other novel potassium channel modulators which target Kv1.5 or $Kv_{(ur)}$ have been described for the treatment of cardiac arrhythmias, these include biphenyls (Peukert et al 2003), thiophene carboxylic acid amides (WO0248131), bisaryl derivatives (WO0244137, WO0246162), carbonamide derivatives (WO0100573, WO0125189), anthranillic acid amides (WO2002100825, WO02088073, WO02087568), dihydropyrimidines (WO0140231), cycloakyl derivatives (WO03063797), indane derivatives (WO0146155, WO9804521), tetralin benzocycloheptane derivatives (WO9937607), thiazolidone and metathiazanone derivatives (WO9962891), benzamide derivatives (WO0025774), isoquinoline derivatives (WO0224655), pyridazinone derivatives (WO9818475, WO9818476), chroman derivatives (WO9804542), benzopyran derivatives (WO0121610, WO03000675, WO0121609, WO0125224, WO02064581), benzoxazine derivatives (WO0012492), and the novel compound A1998 purified from Ocean material (Xu & Xu, 2000).

Several further publications disclose compounds which are indicated as acting on potassium channels. Thus, U.S. Pat. No. 6,531,495 discloses 2'-aminomethylbiphenyl-2-carboxamides, WO2002/100825 discloses anthranillic acid amides as antiarrhythmics and WO2002/036556 discloses acylaminoalkylbenzenesulfonamides as cardiovascular agents.

Furanopyrimidines have been reported to be useful as folate inhibitors, anti-histamines, muscle relaxants and agrochemicals. Furanopyrimidines have not previously been reported as useful agents for modulating ion channels.

The synthesis of various 4-amino substituted furanopyrimidines has been reported (Antonov et al., 1994) as well as certain 4-benzylamino substituted furanopyrimidines (Belenkii et al., 1993).

Furanopyrimidines substituted in the 5-position with an alkyl group have been identified as pesticides and fungicides. Thus EP459611 discloses a family of 4-phenylethyl derivatives, whilst EP196524 discloses a series of 4-phenoxypropyl derivatives.

Furanopyrimidines substituted with an alkyl group at the 5-position have also been disclosed as having muscle-relaxant activity (JP48081893 and DE1817146).

BRIEF SUMMARY OF THE INVENTION

This invention provides compounds that are potassium channel inhibitors. Specifically, furanopyrimidines with an aromatic or heteroaromatic substituent at the 5-position are disclosed. These compounds are particularly useful for inhib-

DETAILED DESCRIPTION OF THE INVENTION

Thus, in a first aspect, the present invention provides a compound of formula I.

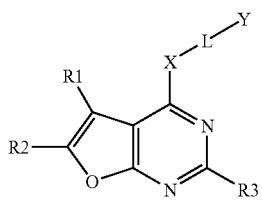

wherein $R_1$ is aryl, heteroaryl, cycloalkyl or alkyl;

$R_2$ is H, alkyl, nitro, —$CO_2R_7$, $CONR_4R_5$ or halo;

$R_3$ is H, $NR_4R_5$, $NR_6C(O)R_8$, halo, trifluoromethyl, alkyl, nitrile or alkoxy;

$R_4$ and $R_5$ may be the same or different, and may be H, alkyl, aryl, heteroaryl or cycloalkyl; or $R_4$ and $R_5$ may together form a saturated, unsaturated or partially saturated 4 to 7 member ring, wherein said ring may optionally comprise one or more further heteroatoms selected from N, O or S;

X is O, S or $NR_6$;

$R_6$ is H or alkyl;

$R_7$ is hydrogen, methyl or ethyl;

$R_8$ is methyl or ethyl;

L is $(CH_2)_n$, where n is 1, 2 or 3; and

Y is aryl, a heterocyclic group, alkyl, alkenyl or cycloalkyl;

or pharmaceutically acceptable salts thereof;

As used herein, an alkyl group or moiety is typically a linear or branched alkyl group or moiety containing from 1 to 6 carbon atoms, such as a $C_1$-$C_4$ alkyl group or moiety, for example methyl, ethyl, n-propyl, i-propyl, butyl, i-butyl and t-butyl. An alkyl group or moiety may be unsubstituted or substituted at any position. Typically, it is unsubstituted or carries one or two substituents. Suitable substituents include halogen, cyano, nitro, $NR_9R_{10}$, alkoxy, hydroxyl, unsubstituted aryl, unsubstituted heteroaryl, $CO_2R_7$, $C(O)NR_9R_{10}$, $NR_6C(O)R_8$ and $SO_2NR_9R_{10}$.

As used herein, an aryl group is typically a $C_6$-$C_{10}$ aryl group such as phenyl or napthyl. A preferred aryl group is phenyl. An aryl group may be unsubstituted or substituted at any position. Typically, it carries 1, 2, 3 or 4 substituents. Suitable substituents include cyano, halogen, nitro, trifluoromethyl, alkyl, alkylthio, alkoxy, $NR_9R_{10}$, $CO_2R_7$, $C(O)NR_9R_{10}$, $NR_6C(O)R_8$ and $SO_2NR_9R_{10}$ and hydroxyl.

As used herein, a heterocyclic group is a heteroaryl group, typically a 5- to 10-membered aromatic ring, such as a 5- or 6-membered ring, containing at least one heteroatom selected from O, S and N. Examples include pyridyl, pyrazinyl, pyrimidinyl, pyridazinyl, furanyl, thienyl, pyrazolidinyl, pyrrolyl and pyrazolyl groups. Preferred heteroaryl groups are furanyl, thienyl and pyridyl. Examples of polycyclic heterocycles include indolyl, benzofuranyl, benzothiophenyl and benzodioxolyl. Non-aryl heterocyclic groups are also included, such as tetrahydrofuranyl or pyrrolidinyl. A heterocyclic group may be unsubstituted or substituted at any position. Suitable substituents include cyano, nitro, halogen, alkyl, alkylthio, alkoxy, $NR_9R_{10}$, $CO_2R_7$, $C(O)NR_9R_{10}$, $NR_6C(O)R_8$ and $SO_2NR_9R_{10}$ and hydroxyl.

$R_9$ and $R_{10}$ can be the same or different, and may be selected from H, unsubstituted alkyl, unsubstituted aryl, unsubstituted heteroaryl, unsubstituted cycloalkyl, aminoethyl, methylaminoethyl, dimethylaminoethyl, hydroxyethyl, alkoxyethyl, or $R_9$ and $R_{10}$ may together form a saturated, unsaturated or partially saturated 4 to 7 member ring.

When $R_4$ and $R_5$ or $R_9$ and $R_{10}$ together form a saturated, unsaturated or partially saturated 4 to 7 member ring, the ring may optionally comprise one, two, or three further heteroatoms.

As used herein, alkoxy means $C_{1-3}$ alkoxy, cycloalkyl means $C_{3-6}$ cycloalkyl and halogen means Cl, F, Br, or I, preferably Cl, F or Br.

Preferred compounds of formula I are those wherein $R_1$ is aryl or heteroaryl, $R_2$ is H or alkyl, $R_3$ is H, $NR_4R_5$, alkoxy or alkyl, X is O or $NR_6$, $R_6$ is H, n is 1 or 2 and Y is alkyl, cycloalkyl, aryl or heteroaryl.

More preferred compounds of formula I are those wherein $R_1$ is aryl or heteroaryl, $R_2$ is H or methyl, $R_3$ is H, $NR_4R_5$, alkoxy or alkyl, X is $NR_6$, $R_6$ is H, n is 1 and Y is aryl or heteroaryl.

Preferably Y is phenyl, furanyl, thienyl or pyridyl. More preferably Y is optionally substituted phenyl, furan-2-yl or pyridine-2-yl.

Preferred compounds include:

5-Phenyl-N-(pyridin-2'-ylmethyl)furo[2,3-d]pyrimidin-4-amine, 5-(4-Chlorophenyl)-N-(pyridin-2'-ylmethyl)furo[2,3-d]pyrimidin-4-amine, 6-Methyl-5-phenyl-N-(pyridin-2'-ylmethyl)furo[2,3-d]pyrimidin-4-amine, (2-Morpholin-4-yl-5-phenyl-furo[2,3-d]pyrimidin-4-yl)-pyridin-2-ylmethyl-amine, 2-((2-Hydroxyethyl)-{5-Phenyl-4-[(pyridine-2-ylmethyl)-amino]-furo[2,3-d]pyrimidin-2-yl}-amino)-ethanol, 2-((2-Hydroxyethyl)-{5-(4-Fluoro-phenyl)-4-[(pyridine-2-ylmethyl)-amino]-furo[2,3-d]pyrimidin-2-yl}-amino)-ethanol, $N^2$-(2-Methoxyethyl)-5-phenyl-$N^4$-pyridin-2-ylmethyl-furo[2,3-d]pyrimidine-2,4-diamine, 2-{5-Phenyl-4-[(pyridin-2-ylmethyl)-amino]furo[2,3-d]pyrimidin-2-ylamino}-propane-1,3-diol, $N^2,N^2$-Dimethyl-5-phenyl-$N^4$-pyridin-2-ylmethyl-furo[2,3-d]pyrimidine-2,4-diamine, $N^2,N^2$-Dimethyl-$N^4$-(6-methyl-pyridin-2-ylmethyl)-5-phenyl-furo[2,3-d]pyrimidine-2,4-diamine, or

[2-(2-Methoxyethoxy)-5-phenyl-furo[2,3-d]pyrimidin-4-yl]-pyridin-2ylmethylamine, and pharmaceutically acceptable salts thereof.

Compounds of formula I wherein $R_3$=H are conveniently synthesised from a compound of formula II by reaction with a suitable nucleophile HX-L-Y (where X, Y and L are as defined herein), optionally in the presence of a solvent, and optionally at elevated temperature. Preferably the solvent (if present) is an alcohol, preferably ethanol. If a solvent is present the reaction is carried out at the reflux temperature of the solvent. Optionally the reaction may be carried out in a microwave reactor.

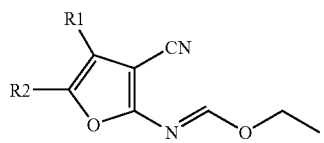

II

A compound of formula II may be obtained from a compound of formula III by reaction with a trialkyl orthoformate in a suitable solvent or no solvent, and with heating. Preferably the trialkyl orthoformate is triethyl orthoformate. Preferably a solvent is present. Suitable solvents include acetic anhydride. When a solvent is present the reaction is carried out at reflux temperature.

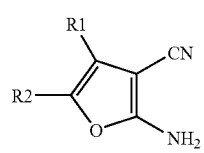

III

Compounds of formula III may be obtained by the reaction of a compound of formula IV with malononitrile. The reaction may be carried out in the presence of a suitable solvent and a base. Preferably the solvent is ethanol and the reaction is carried out under reflux conditions. Preferably a base is present. Suitable bases include hindered organic amines such as triethylamine.

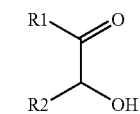

IV

A compound of formula IV can be prepared by reaction of a compound of formula V under oxidative conditions. Preferred oxidizing agents include [bis(trifluoroacetoxy) iodo]benzene. The reaction is preferably carried out in the presence of a solvent and an organic acid. Suitable solvents include acetonitrile. Suitable organic acids include trifluoroacetic acid. When a solvent is present the reaction is carried out at reflux temperature.

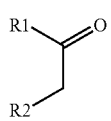

V

In an alternative synthesis of compounds of formula I, particularly applicable when $R_3$ is a substituent other than H, a suitable nucleophile $R_3H$ is reacted with a compound of formula VI. Preferably the reaction is carried out in the presence of a base and a solvent. Optionally the reaction may be carried out in a microwave reactor.

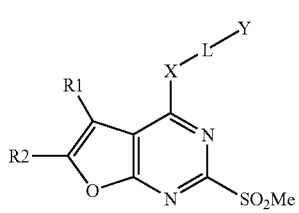

VI

A compound of formula VI is conveniently prepared from a compound of formula VII. Suitable reaction conditions include the use of a nucleophile HX-L-Y in the presence of a base and a solvent. Preferably the base is a hindered organic amine base such as triethylamine and the solvent is an alcohol such as ethanol.

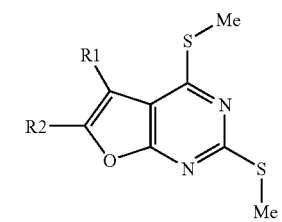

VII

A compound of formula VII may be prepared by oxidation of a compound of formula VIII. Suitable conditions include the use of a peroxide reagent in an organic acid. Preferably the peroxide reagent is hydrogen peroxide and the organic acid is acetic acid.

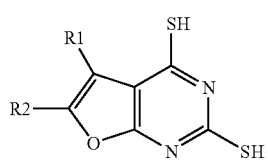

VIII

A compound of formula VIII may be prepared by reaction of a compound of formula IX under alkylating conditions. Suitable conditions include the use of a methyl iodide, under basic conditions. Preferably the basic conditions comprise a metal hydroxide in a mixture of alcohol and water. Preferably the alcohol is ethanol, the metal hydroxide is potassium hydroxide, and the alkyl halide is methyl iodide.

IX

A compound of formula IX may be conveniently prepared by reaction of a compound of formula III with potassium ethyl xanthate. Preferably the reaction is carried out in alcohol. Preferably the alcohol is butanol.

In a further method, particularly applicable to examples wherein $R_3$ is a functionalized alkyl substituent, a compound of formula X is reacted with a suitable nucleophile HX-L-Y. The reaction is carried out in the presence of a base and in a solvent. The base is preferably an organic amine base such as triethylamine and the solvent is preferably an alcohol such as ethanol. The reaction is carried out at the reflux temperature of the solvent. Alternatively the reaction may be carried out with microwave heating.

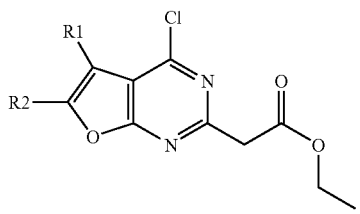

X

A compound of formula X may be prepared by reaction of a compound of formula XI with a suitable chlorinating reagent. Preferably the chlorinating reagent is thionyl chloride, phosphorous oxychloride or diphenylphosphinic chloride. Preferably the reaction is carried out in the presence of a base such as an amine base. Preferred bases include triethylamine and diethylaniline. Optionally the base may also serve as the solvent. The reaction is carried out at 60-100° C.

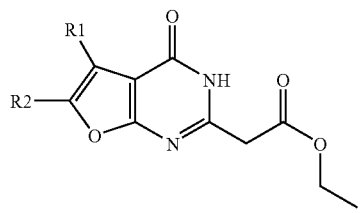

XI

Compounds of formula XI may be prepared by reaction of a compound of formula XII under acidic conditions in a solvent. Preferably the acid is an inorganic acid such as hydrochloric acid and the solvent is an organic solvent such as dioxane. The reaction is carried out at or below the reflux temperature of the solvent.

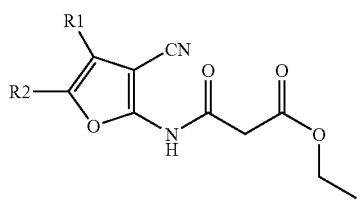

XII

Compounds of formula XII are readily prepared from compounds of formula III by reaction with ethyl malonyl chloride. Preferably the reaction is carried out with cooling and in the presence of a base and an organic solvent. Preferably the base is triethylamine and the solvent is tetrahydrofuran, and the reaction is carried out at below 5° C.

It is understood that compounds of formula I wherein $R_3$ is a carboethoxy group may undergo functional group transformation of the ester moiety using methods familiar to those skilled in the art. In a preferred instance such compounds may undergo amidation by reaction with an alkyl or dialkylamine. In another preferred instance compounds of formula I wherein $R_3$ is a 1-hydroxyethyl group can be prepared by the reaction with a reducing agent such as diisobutylaluminium hydride or lithium aluminium hydride. In a further instance compounds of formula I wherein $R_3$ is a carboethoxy group may be reacted with a dialkyl carbonate under basic conditions to provide a compound of formula I wherein $R_3$ is a dialkylmalonyl group. Such compounds may be reduced, preferably with a reducing agent such as diisobutylaluminium hydride or lithium aluminium hydride, to provide compounds of formula I wherein $R_3$ is a propanediol group.

Many of the starting materials referred to in the reactions described above are available from commercial sources or can be made by methods cited in the literature references. Synthetic methods can also be found in reviews; thiophenes for example can be found in references cited in Comprehensive Heterocyclic Chemistry, Eds Katritzky, A. R., Rees, C. R., (4), 863-934, and Comprehensive Heterocyclic Chemistry (II), Eds Katritzky, A. R., Rees, C. W., Scriven, E. F. V., (2), 607-678.

Suitable starting materials include:

| Material | Reference | Supplier |
| --- | --- | --- |
| 4'-Fluoroacetophenone | F-320-7 | Aldrich |
| 1-(4-Fluorophenyl)-propan-1-one | F-12,841-4 | Aldrich |
| Acetophenone | A1 070-1 | Aldrich |
| 2-(Aminomethyl)pyridine | A6,520-4 | Aldrich |
| 2-Furfurylamine | F20009 | Aldrich |
| 4'-Chloroacetophenone | C1,970-8 | Aldrich |
| 1-(3,4-Dimethoxyphenyl)ethanone | 15,663-9 | Aldrich |
| 1-(1,3-Benzodioxol-6-yl)ethanone | 17,902-7 | Aldrich |
| Propiophenone | P5,160-5 | Aldrich |
| Malononitrile | 12527-1000 | Acros |
| Ethyl malonyl chloride | 252-934-5 | Lancaster |

As discussed herein, the compounds of the invention are useful in the treatment of various conditions. Thus, in a second aspect, the present invention provides a pharmaceutical formulation comprising at least one compound of the invention and optionally one or more excipients, carriers or diluents, wherein said compound has the formula:

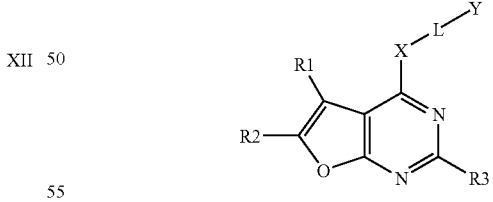

I

Wherein
$R_1$ is aryl, heteroaryl, cycloalkyl or alkyl;
$R_2$ is H, alkyl, nitro, —$CO_2R_7$, $CONR_4R_5$ or halo;
$R_3$ is H, $NR_4R_5$, $NR_6C(O)R_8$ halo, trifluoromethyl, alkyl, nitrile or alkoxy;
$R_4$ and $R_5$ may be the same or different, and may be H, alkyl, aryl, heteroaryl or cycloalkyl; or $R_4$ and $R_5$ may together form a saturated, unsaturated or partially saturated 4 to 7 member ring, wherein said ring may optionally comprise one or more further heteroatoms selected from N, O or S;
X is O, S or $NR_6$;

R₆ is H or alkyl;
R₇ is hydrogen, methyl or ethyl;
R₈ is methyl or ethyl;
L is (CH₂)ₙ, where n is 1, 2 or 3; and
Y is aryl, a heterocyclic group, alkyl, alkenyl or cycloalkyl; or pharmaceutically acceptable salts thereof, The compositions of the invention may be presented in unit dose forms containing a predetermined amount of each active ingredient per dose. Such a unit may be adapted to provide 5-100 mg/day of the compound, preferably either 5-15 mg/day, 10-30 mg/day, 25-50 mg/day 40-80 mg/day or 60-100 mg/day. For compounds of formula I, doses in the range 100-1000 mg/day are provided, preferably either 100-400 mg/day, 300-600 mg/day or 500-1000 mg/day. Such doses can be provided in a single dose or as a number of discrete doses. The ultimate dose will of course depend on the condition being treated, the route of administration and the age, weight and condition of the patient and will be at the doctor's discretion.

The compositions of the invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 3(6), 318 (1986).

Pharmaceutical formulations adapted for topical administration may be formulated as ointments, creams, suspensions, lotions, powders, solutions, pastes, gels, sprays, aerosols or oils.

For applications to the eye or other external tissues, for example the mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administration to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Preferred unit dosage formulations are those containing a daily dose or sub-dose, as herein above recited, or an appropriate fraction thereof, of an active ingredient.

It should be understood that in addition to the ingredients particularly mentioned above, the formulations may also include other agents conventional in the art having regard to the type of formulation in question, for example those suitable for oral administration may include flavouring agents.

In a further aspect the present invention provides a compound, or a pharmaceutical composition comprising said compound for use in medicine, wherein said compound has the formula:

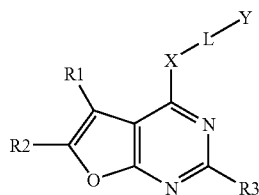

Wherein
R₁ is aryl, heteroaryl, cycloalkyl or alkyl;
R₂ is H, alkyl, nitro, CO₂R₇, CONR₄R₅ or halo;
R₃ is H, NR₄R₅, NR₆C(O)R₈ halo, trifluoromethyl, alkyl, nitrile or alkoxy;
R₄ and R₅ may be the same or different, and may be H, alkyl, aryl, heteroaryl or cycloalkyl; or R₄ and R₅ may together form a saturated, unsaturated or partially saturated 4 to 7 member ring, wherein said ring may optionally comprise one or more further heteroatoms selected from N, O or S;
X is O, S or NR₆;
R₆ is H or alkyl;
R₇ is hydrogen, methyl or ethyl;
R₈ is methyl or ethyl;
L is (CH₂)ₙ, where n is 1, 2 or 3; and
Y is aryl, a heterocyclic group, alkyl, alkenyl or cycloalkyl; or pharmaceutically acceptable salts thereof;
Preferably, the compound is a compound of the first aspect.

The compositions of the invention can be used to treat conditions which require inhibition of potassium channels, for example in the treatment of arrythmia. Thus, in further aspects, the present invention provides:

(i) a method of treating or preventing a disorder which requires potassium channel inhibition, eg arrythmia, comprising administering to a subject an effective amount of at least one compound or of a pharmaceutical composition comprising said at least one compound and optionally one or more excipients, diluents and/or carriers wherein said compound has the formula:

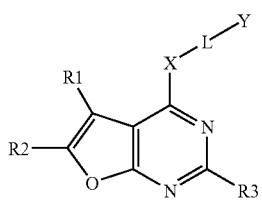

Wherein $R_1$ is aryl, heteroaryl, cycloalkyl or alkyl;

$R_2$ is H, alkyl, nitro, $CO_2R_7$, $CONR_4R_5$ or halo;

$R_3$ is H, $NR_4R_5$, $NR_6C(O)R_8$ halo, trifluoromethyl, alkyl, nitrile or alkoxy;

$R_4$ and $R_5$ may be the same or different, and may be H, alkyl, aryl, heteroaryl or cycloalkyl; or $R_4$ and $R_5$ may together form a saturated, unsaturated or partially saturated 4 to 7 member ring, wherein said ring may optionally comprise one or more further heteroatoms selected from N, O or S;

X is O, S or $NR_6$;

$R_6$ is H or alkyl;

$R_7$ is hydrogen, methyl or ethyl;

$R_8$ is methyl or ethyl;

L is $(CH_2)_n$, where n is 1, 2 or 3; and

Y is aryl, a heterocyclic group, alkyl, alkenyl or cycloalkyl; or pharmaceutically acceptable salts thereof; and (ii) the use of a compound of the invention in the manufacture of a medicament for use in potassium channel inhibition; wherein the compound has the formula:

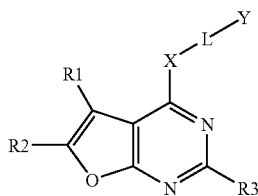

Wherein $R_1$ is aryl, heteroaryl, cycloalkyl or alkyl;

$R_2$ is H, alkyl, nitro, $CO_2R_7$, $CONR_4R_5$ or halo;

$R_3$ is H, $NR_4R_5$, $NR_6C(O)R_8$ halo, trifluoromethyl, alkyl, nitrile or alkoxy;

$R_4$ and $R_5$ may be the same or different, and may be H, alkyl, aryl, heteroaryl or cycloalkyl; or $R_4$ and $R_5$ may together form a saturated, unsaturated or partially saturated 4 to 7 member ring, wherein said ring may optionally comprise one or more further heteroatoms selected from N, O or S;

X is O, S or $NR_6$;

$R_6$ is H or alkyl;

$R_7$ is hydrogen, methyl or ethyl;

$R_8$ is methyl or ethyl;

L is $(CH2)n$, where n is 1, 2 or 3; and

Y is aryl, a heterocyclic group, alkyl, alkenyl or cycloalkyl; or pharmaceutically acceptable salts thereof.

In particular, the medicament is for use in the treatment or prevention of arrhythmia.

Preferably the compounds are compounds of the first aspect.

EXAMPLES

Using the information outlined herein the following compounds can be synthesised which are given by way of example only. The pharmacological profile of compounds of the present invention can readily be assessed by those skilled in the art using routine experimentation, such as procedures and techniques illustrated herein and described in detail in Ford et al., 2002.

Example 1

1-(4-Fluorophenyl)-2-hydroxyethanone

Under a nitrogen atmosphere, a stirred solution of 4'-fluoroacetophenone (1.15 g, 8.32 mmol) in acetonitrile (42 ml) was treated with [bis(trifluoroacetoxy)iodo]benzene (7.16 g, 16.6 mmol) followed by water (8.3 ml) and trifluoroacetic acid (1.3 ml). The resultant solution was heated under reflux for 2 hr before standing overnight at ambient temperature. The solvent was then removed in vacuo; water (30 ml) was added and the mixture extracted with dichloromethane (3×30 ml). The combined extracts were washed with saturated sodium hydrogen carbonate solution (30 ml) followed by brine (30 ml) and dried ($MgSO_4$). The solvent was removed in vacuo to give the crude 1-(4-fluorophenyl)-2-hydroxyethanone which was purified by flash chromatography (silica) eluting with ethyl acetate and 40°-60° C. petroleum ether (3:1) to give a white solid (0.55 g).

Examples 2 to 7

The compounds set out below were prepared in the same way as in Example 1, using the appropriate starting materials.

| Example | Compound |
| --- | --- |
| 2 | 2-Hydroxy-1-phenylethanone |
| 3 | 1-(4-Chlorophenyl)-2-hydroxyethanone |
| 4 | 1-(3,4-Dimethoxyphenyl)-2-hydroxyethanone |
| 5 | 1-(1,3-Benzodioxol-5-yl)-2-hydroxyethanone |
| 6 | 2-Hydroxy-1-phenylpropan-1-one |
| 7 | 1-(4-Fluorophenyl)-2-hydroxypropan-1-one |

Example 8

2-Amino-4-(4-fluorophenyl)-3-furonitrile

A solution of malononitrile (0.31 g, 4.65 mmol) and triethylamine (0.65 ml, 4.65 mmol) in methanol (5 ml) was added drop-wise to a stirred suspension of 2-hydroxy-4'-fluoroacetophenone (0.65 g, 4.22 mmol) in methanol (16 ml) under a nitrogen atmosphere at ambient temperature. When the addition was complete, the mixture was stirred for 18 hr at ambient temperature. The solvent was then removed in vacuo, water (50 ml) was then added to the residue and the mixture was extracted with dichloromethane (3×50 ml). The combined extracts were dried ($MgSO_4$) and the solvent removed in vacuo to give the crude 2-amino-4-(4'-fluorophenyl)-3-furonitrile which was partially purified by flash chromatography (silica) eluting with dichloromethane and ethyl acetate (1:1). This gave a 3.5:1 mixture of the product and 2-hydroxy-4'-fluoroacetophenone (0.60 g), which was used without further purification.

Examples 9 to 13

The compounds set out below were prepared in the same way as in Example 8, using the appropriate starting materials.

| Example | Compound |
| --- | --- |
| 9 | 2-Amino-4-phenyl-3-furonitrile |
| 10 | 2-Amino-4-(4'-chlorophenyl)-3-furonitrile |
| 11 | 2-Amino-4-(3',4'-dimethoxyphenyl)-3-furonitrile |
| 12 | 2-Amino-4-(1',3'-benzodioxol-5-yl)-3-furonitrile |
| 13 | 2-Amino-5-methyl-4-phenyl-3-furonitrile |
| 14 | 2-Amino-4-(4-fluorophenyl)-5-methylthiophene-3-carbonitrile |

Example 15

Ethyl 3-cyano-4-(4-fluorophenyl)-2-furylimidoformate

A stirred mixture of 2-amino-4-(4-fluorophenyl)-3-furonitrile (0.27 g, 1.36 mmol) and triethyl orthoformate (0.95 ml) was treated with acetic anhydride (0.65 ml) and then heated under reflux for 4 hr. The solvents were then removed in vacuo to give Ethyl 3-cyano-4-(4-fluorophenyl)-2-furylimidoformate as a brown solid (0.35 g), which was used without further purification.

Examples 16 to 20

The compounds set out below were prepared in the same way as in Example 15, using the appropriate starting materials.

| Example | Compound |
| --- | --- |
| 16 | Ethyl 3-cyano-4-phenyl-2-furylimidoformate |
| 17 | Ethyl 4-(4-chlorophenyl)-3-cyano-2-furylimidoformate |
| 18 | Ethyl 3-cyano-4-(3,4-dimethoxyphenyl)-2-furylimidoformate |
| 19 | Ethyl 4-(1,3-benzodioxol-5-yl)-3-cyano-2-furylimidoformate |
| 20 | Ethyl 3-cyano-5-methyl-4-phenyl-2-furylimidoformate |

Example 21

5-(4-Fluorophenyl)-N-(pyridin-2-ylmethyl)furo[2,3-d]pyrimidin-4-amine

A stirred reaction mixture of the crude ethyl 3-cyano-4-(4-fluorophenyl)-2-furylimidoformate (0.35 g, 1.36 mmol) and pyridin-2-yl-methylamine (0.16 ml, 1.50 mmol) in ethanol (3.5 ml) was heated under reflux for 4 hr. The resultant mixture was cooled to ambient temperature and the solvent was removed in vacuo. The residue was purified by flash chromatography (silica) eluting with ethyl acetate and dichloromethane (1:1) to give 5-(4-fluorophenyl)-N-(pyridin-2-ylmethyl)furo[2,3-d]pyrimidin-4-amine (0.15 g) as an off-white solid, m.pt. 162'-164° C.

Examples 22 to 26

The compounds set out below were prepared in the same way as in Example 21, using the appropriate starting materials.

| Example | Compound |
| --- | --- |
| 22 | 5-Phenyl-N-(pyridin-2'-ylmethyl)furo[2,3-d]pyrimidin-4-amine |
| 23 | 5-(4-Chlorophenyl)-N-(pyridin-2'-ylmethyl)furo[2,3-d]pyrimidin-4-amine |
| 24 | 5-(3,4-Dimethoxyphenyl)-N-(pyridin-2'-ylmethyl)furo[2,3-d]pyrimidin-4-amine |
| 25 | 5-(1,3-Benzodioxol-5'-yl)-N-(pyridin-2'-ylmethyl)furo[2,3-d]pyrimidin-4-amine |
| 26 | 6-Methyl-5-phenyl-N-(pyridin-2'-ylmethyl)furo[2,3-d]pyrimidin-4-amine |

Example 27

5-Phenyl-1H-furo[2,3-d]pyrimidine-2,4-dithione

A stirred mixture of 2-amino-4-phenyl-furan-3-carbonitrile (5.0 g, 0.027 mol) and potassium ethyl xanthate (4.5 g, 0.027 mol) in butan-1-ol (25 ml) was heated for 2 hr at 110° C. After cooling to ambient temperature, the solid was filtered off, washed with a little butan-1-ol and dissolved in water (100 ml). The solution was then acidified with glacial acetic acid to give a light-brown precipitate. This was filtered off, washed with water and dried in vacuo to give the crude 5-phenyl-1H-furo[2,3-d]pyrimidine-2,4-dithione (3.0 g) which was used without further purification.

Examples 28 to 29

The compounds set out below were prepared in the same way as in Example 27, using the appropriate starting materials.

| Example | Compound |
| --- | --- |
| 28 | 6-Methyl-5-phenyl-1H-furo[2,3-d]pyrimidine-2,4-dithione |
| 29 | 5-(4-Fluorophenyl)-6-methyl-1H-furo[2,3-d]pyrimidine-2,4-dithione |

Example 30

2,4-Bis-methylsulfanyl-5-phenyl-furo[2,3-d]pyrimidine

A stirred mixture of 5-phenyl-1H-furo[2,3-d]pyrimidine-2,4-dithione (3.0 g, 0.012 mol) in ethanol (100 ml) and potassium hydroxide (1.4 g, 0.024 mol) in water (25 ml) was treated with iodomethane (3.6 g, 1.6 ml, 0.025 mol). After 3 hr at ambient temperature, the mixture was diluted with water (250 ml) and extracted with dichloromethane (3×100 ml). The combined extracts were dried (MgSO$_4$) and the solvent removed in vacuo to give the crude 2,4-bis-methylsulfanyl-5-phenyl-furo[2,3-d]pyrimidine which was purified by flash chromatography (silica) eluting with dichloromethane to give a brown solid (3.0 g).

Examples 31 to 32

The compounds set out below were prepared in the same way as in Example 30, using the appropriate starting materials.

| Example | Compound |
|---|---|
| 31 | 2,4-Bis-methylsulfanyl-6-methyl-5-phenyl-1H-furo[2,3-d]pyrimidine |
| 32 | 2,4-Bis-methylsulfanyl-5-(4-fluorophenyl)-6-methyl-1H-furo[2,3-d]pyrimidine |

Example 33

2,4-Bis-methylsulfonyl-5-phenyl-furo[2,3-d]pyrimidine

A stirred suspension of 2,4-bis-methylsulfanyl-5-phenyl-furo[2,3-d]pyrimidine (1.5 g, 5.21 mmol) in glacial acetic acid (15 ml) was treated with hydrogen peroxide (3.6 ml of a 27.5% aqueous solution, 33.3 mmol). After 2 hr at ambient temperature, the mixture was heated to obtain an homogenous solution and then stirred at ambient temperature for 18 hr. The reaction mixture was then diluted with water (50 ml) and extracted with dichloromethane (3×50 ml). The combined extracts were washed with an aqueous solution of sodium metabisulfite (2×50 ml) followed by saturated aqueous sodium hydrogen carbonate (50 ml) before being dried (MgSO$_4$). The solvent was removed in vacuo to give the crude 2,4-bis-methylsulfonyl-5-phenyl-furo[2,3-d]pyrimidine which was purified by flash chromatography (silica) eluting with ethyl acetate to give a white solid (0.5 g).

Examples 34 to 35

The compounds set out below were prepared in the same way as in Example 33, using the appropriate starting materials.

| Example | Compound |
|---|---|
| 34 | 2,4-Bis-methylsulfonyl-6-methyl-5-phenyl-1H-furo[2,3-d]pyrimidine |
| 35 | 2,4-Bis-methylsulfonyl-5-(4-fluorophenyl)-6-methyl-1H-furo[2,3-d]pyrimidine |

Example 36

(2-Methanesulfonyl-5-phenyl-furo[2,3-d]pyrimidin-4-yl)-pyridin-2-ylmethylamine

A mixture of 2,4-bis-methylsulfonyl-5-phenyl-furo[2,3-d]pyrimidine (54 mg, 0.153 mmol), triethylamine (17 mg, 0.168 mmol) and 2-(aminomethyl)pyridine (18 mg, 0.168 mmol) in propan-2-ol (5 ml) was warmed to obtain a solution and stirred at ambient temperature for 2.5 hr. Water (50 ml) was then added and the mixture was extracted with dichloromethane (3×30 ml). The combined extracts were dried (MgSO$_4$) and the solvent removed in vacuo to give the crude (2-methanesulfonyl-5-phenyl-furo[2,3d]pyrimidin-4-yl)-pyridin-2-ylmethylamine which was purified by flash chromatography (silica) eluting with 40'-60° C. petroleum ether followed by ethyl acetate to give a white solid (17 mg), m.pt. 171-173° C.

Examples 37 to 40

The compounds set out below were prepared in the same way as in Example 36, using the appropriate starting materials.

| Example | Compound |
|---|---|
| 37 | (2-Methanesulfonyl-5-phenyl-furo[2,3-d]pyrimidin-4-yl)-(6-methylpyridin-2-ylmethyl)-amine |
| 38 | Furan-2-ylmethyl-(2-methanesulfonyl-5-phenyl-furo[2,3-d]pyrimidin-4-yl)-amine |
| 39 | (2-Methanesulfonyl-6-methyl-5-phenyl-furo[2,3-d]pyrimidin-4-yl)-pyridin-2-ylmethylamine |
| 40 | [5-(4-Fluorophenyl)-2-methanesulfonyl-6-methyl-furo[2,3-d]pyrimidin-4-yl]-pyridin-2-ylmethylamine |

Example 41

N$^2$-(2-Methoxyethyl-N$^4$-pyridin-2-ylmethyl-furo[2,3-d]pyrimidine-2,4-diamine A stirred mixture of (2-methanesulfonyl-5-phenyl-furo[2,3d]pyrimidin-4-yl)-pyridin-2-ylmethylamine (50 mg, 0.132 mmol), triethylamine (15 mg, 0.145 mmol) and 2-methoxyethylamine (10 mg, 0.197 mmol) in ethanol (1 ml) was heated by microwave irradiation at 180° C. for 30 mins. The resultant solution was diluted with water (30 ml) and extracted with dichloromethane (3×30 ml). The combined extracts were dried (MgSO$_4$) and the solvent removed in vacuo to give the crude N$^2$-(2-methoxyethyl)-5-phenyl-N$^4$-pyridin-2-ylmethyl-furo[2,3-d]pyrimidine-2,4-diamine which was purified by flash chromatography (silica) eluting with dichloromethane followed by ethyl acetate and dichloromethane (2:1) to give an off-white solid (26 mg), m.pt. 96-98° C.

Examples 42 to 45

The compounds set out below were prepared in the same way as in Example, 41 using the appropriate starting materials.

| Example | Compound |
|---------|----------|
| 42 | (2-Morpholin-4-yl-5-phenyl-furo[2,3-d]pyrimidin-4-yl)-puridin-2-ylmethyl-amine |
| 43 | 2-((2-Hydroxyethyl)-{5-Phenyl-4-[(pyridine-2-ylmethyl)-amino]-furo[2,3-d]pyrimidin-2-yl}-amino)-ethanol |
| 44 | 2-{5-Phenyl-4-[(pyridin-2-ylmethyl)-amino]furo[2,3-d]pyrimidin-2-ylamino}-propane-1,3-diol |
| 45 | 2-((2-Hydroxyethyl)-{5-(4-fluorophenyl)-4-[(pyridine-2-ylmethyl)-amino]-furo[2,3-d]pyrimidin-2-yl}-amino)-ethanol |

Example 46

$N^2,N^2$-Dimethyl-5-phenyl-$N^4$-pyridin-2-ylmethyl-furo[2,3-d]pyrimidine-2,4-diamine Ethanol (1 ml) was saturated with dimethylamine and (2-methanesulfonyl-5-phenyl-furo[2,3d]pyrimidin-4-yl)-pyridin-2-ylmethylamine (50 mg, 0.132 mmol) was added. The mixture was then stirred and heated by microwave irradiation at a pressure of 250 psi for 30 mins, the temperature reaching a maximum of 138° C. The resultant solution was then diluted with water (50 ml) and extracted with dichloromethane (3×50 ml). The combined extracts were dried (MgSO$_4$) and the solvent removed in vacuo to give the crude $N^2,N^2$-dimethyl-5-phenyl-$N^4$-pyridin-2-yl methyl-furo[2,3-d]pyrimidine-2,4-diamine which was purified by flash chromatography (silica) eluting with dichloromethane followed by dichloromethane and ethyl acetate (9:1) to give an off-white solid (19 mg), m.pt. 108-110° C.

Examples 47 to 50

The compounds set out below were prepared in the same way as in Example 45, using the appropriate starting materials.

| Example | Compound |
|---------|----------|
| 47 | $N^2,N^2$-Dimethyl-$N^4$-(6-methyl-pyridin-2-ylmethyl)-5-phenyl-furo[2,3-d]pyrimidine-2,4-diamine |
| 48 | $N^4$-Furan-2-ylmethyl-$N^2,N^2$-dimethyl-5-phenyl-furo[2,3-d]pyrimidine-2,4-diamine |
| 49 | 6,$N^2,N^2$-Trimethyl-5-phenyl-N4-pyridin-2-ylmethyl-furo[2,3-d]pyrimidine-2,4-diamine |
| 50 | 5-(4-Fluorophenyl)-6,$N^2,N^2$-trimethyl-$N^4$-pyridin-2-ylmethyl-furo[2,3-d]pyrimidine-2,4-diamine |

Example 51

[2-(2-Methoxyethoxy)-5-phenyl-furo[2,3-d]pyrimidin-4-yl]-pyridin-2-ylmethylamine Stirred 2-methoxyethanol (1 ml) was treated with 60% sodium hydride (10 mg) followed, after 10 mins, by (2-methanesulfonyl-5-phenyl-furo[2,3d]pyrimidin-4-yl)-pyridin-2-ylmethylamine (50 mg, 0.132 mmol) and heated by microwave irradiation for 30 mins at 150° C. The resultant solution was then diluted with water (50 ml) and extracted with dichloromethane (3×50 ml). The combined extracts were dried (MgSO$_4$) and the solvent removed in vacuo to give the crude [2-(2-methoxyethoxy)-5-phenyl-furo[2,3-d]pyrimidin-4-yl]-pyridin-2-ylmethylamine which was purified by flash chromatography (silica) eluting with 40'-60° C. petroleum ether followed by 40'-60° C. petroleum ether and ethyl acetate (1:1) to give an off-white solid (30 mg), m.pt. 97-99° C.

Example 52

Ethyl 3-[(3-cyano-4-phenyl-2-furyl)amino]-3-oxopropanoate

Ethyl malonyl chloride (3.8 ml, 29.89 mmol) was added dropwise to a solution of 2-amino-4-phenyl-3-furonitrile (5 g, 27.17 mmol) and triethylamine (4.2 ml, 29.89 mmol) in THF (30 ml) maintaining temperature below 5° C. under nitrogen. This was allowed to warm up to room temperature and stirred for 2 hr. The reaction mixture was diluted with water and extracted with DCM. The organic layers were combined and washed with brine and dried over MgSO$_4$. The solution was filtered and solvent removed under reduced pressure. The residue was purified by column chromatography using DCM isolating an orange oil (3.7 g, 46%).

Example 53

Ethyl (4-oxo-5-phenyl-3,4-dihydrofuro[2,3-d]pyrimin-2-yl)acetate

3-[(3-Cyano-4-phenyl-2-furyl)amino]-3-oxopropanoate (1.2 g, 4.2 mmol) was added to a solution of 4M hydrogen chloride in dioxane (20 ml) and heated to reflux with stirring for 2 hr. The reaction mixture was cooled to room temperature and poured into saturated sodium hydrogen carbonate solution. The aqueous phase was extracted with DCM. The organic phases were combined and washed with brine and dried over MgSO$_4$. The organic layer was filtered and the solvent was removed under reduced pressure. The residue was purified by column chromatography using DCM to provide a brown solid (0.925 g).

Example 54

Ethyl (4-chloro-5-phenylfuro[2,3-d]pyrimin-2-yl)acetate

Ethyl (4-oxo-5-phenyl-3,4-dihydrofuro[2,3-d]pyrimin-2-yl)acetate (827 mg, 2.79 mmol) was added to a solution of phosphorus oxychloride (13 ml, 139.5 mmol) and diethyl aniline (4.4 ml, 27.8 mmol) and heated to 65C and stirred for 2.5 hr. Phosphorous oxychloride was removed under reduced pressure and the residue was diluted with DCM. The organic layer was washed with water twice and then with saturated sodium hydrogen carbonate solution and finally with brine. The solution was dried over MgSO$_4$ and filtered. Solvent was removed under reduced pressure and the residue was purified by column chromatography (20-100% DCM/40'-60' petrol) to provide an orange oil (100 mg).

Example 55

Ethyl {5-phenyl-4-[(pyridine-2-ylmethyl)amino]furo[2,3-d]pyrimidin-2-yl}-acetate 2-Aminomethyl pyridine (36 microL, 0.347 mmol) was added to a solution of ethyl (4-chloro-5-phenylfuro[2,3-d]pyrimin-2-yl)acetate (100 mg, 0.316 mmol) and triethylamine (48 microL, 0.347 mmol) in ethanol (5 ml) and heated to reflux for 4 hr. The reaction mixture was cooled and diluted with water. The aqueous mixture was extracted three times with DCM. The organic phases were combined and washed with brine then dried over $MgSO_4$. The solvent was removed using reduced pressure and the residue was purified using column chromatography (0-10% ethyl acetate/DCM) to provide a red oil (10 mg).

Example 56

Analytical data for the compounds described is summarized in the table below:

| Example | NMR Spectrum $\delta_H$ (400 MHz; $CDCl_3$; $Me_4Si$), | Mass Spectrum (m/z) | M. Pt. (° C.) |
|---|---|---|---|
| 21 | 4.82(2H, d), 6.76(1H, br s), 7.23(4H, m), 7.48(1H, s), 7.54(2H, m), 7.65(1H, dd), 8.43(1H, m), 8.49(1H, s). | 321(100%, [M+H]+) | 162-164 |
| 22 | 4.85(2H, d), 6.75(1H, br s), 7.20(1H, m), 7.30(1H, s), 7.50(6H, m), 7.65(1H, dd), 8.35(1H, d), 8.45(1H, s). | 303(37%, [M+H]+) | 121-123 |
| 23 | 4.80(2H, d), 6.80(1H, br s), 7.20(1H, m), 7.25(1H, m), 7.50(5H, m), 7.65(1H, dd), 8.40(1H, d), 8.50(1H, s). | 337(100%, [35Cl, M+H]+) | 163-164 |
| 24 | 3.85(3H, s), 4.00(3H, s), 4.80(2H, d), 6.85(1H, br s), 7.00(1H, d), 7.05(2H, m), 7.15(1H, m), 7.25(1H, d), 7.45(1H, s), 7.65(1H, m), 8.40(1H, m), 8.50(1H, s). | 363(100%, [M+H]+) | 146-148 |
| 25 | 4.85(2H, d), 6.07(2H, s), 6.82(1H, br s), 6.96(1H, d), 7.03(2H, dd), 7.19(1H, dd), 7.27(1H, m), 7.45(1H, s), 7.66(1H, m), 8.46(2H, s). | 347(100%, [M+H]+) | 186-188 |
| 26 | 2.43(3H, s), 4.77(2H, d), 6.41(1H, br s), 7.14(1H, m), 7.22(1H, m), 7.49(5H, m), 7.61(1H, m), 8.35(1H, d), 8.41(1H, s). | 317(100%, [M+H]+) | 124-128 |
| 42 | 3.77(8H, m), 4.76(2H, d), 6.22(1H, br s), 7.16(1H, m), 7.24(2H, m), 7.49(5H, m), 7.65(1H, m), 8.44(1H, d). | 388(100%, [M+H]+) | 112-114 |
| 43 | 3.81(4H, m), 3.91(4H, m), 4.30(2H, br s), 4.71(2H, d), 6.50(1H, br t), 7.17(1H, m), 7.26(2H, m), 7.49(5H, m), 7.64(1H, m), 8.40(1H, d). | 406(100%, [M+H]+) | oil |
| 41 | 3.38(3H, s), 3.60(4H, m), 4.76(2H, d), 5.25(1H, br t), 6.24(1H, br s), 7.17(2H, m), 7.25(1H, m), 7.48(5H, m), 7.62(1H, m), 8.42(1H, m). | 376(100%, [M+H]+) | 96-98 |
| 44 | 3.85(2H, br s), 3.90(4H, d), 4.12(1H, m), 4.70(2H, d), 5.72(1H, d), 6.41(1H, br s), 7.15(2H, m), 7.24(1H, m), 7.46(5H, m), 7.62(1H, m), 8.38(1H, d). | 392(100%, [M+H]+) | oil |
| 46 | 3.17(6H, s), 4.79(2H, d), 6.07(1H, br s), 7.16(2H, m), 7.27(1H, d), 7.41(1H, m), 7.47(2H, m), 7.54(2H, m), 7.61(1H, t), 8.45(1H, d). | 346(100%, [M+H]+) | 108-110 |
| 47 | 2.40(3H, s), 3.19(6H, s), 4.76(2H, d), 6.14(1H, br t), 6.99(1H, d), 7.05(1H, d), 7.16(1H, s), 7.40(1H, m), 7.50(5H, m). | 360(100%, [M+H]+) | 52-54 |
| 48 | 3.21(6H, s), 4.68(2H, d), 5.10(1H, br s), 6.17(1H, d), 6.30(1H, m), 7.15(1H, s), 7.33(1H, d), 7.38(1H, m), 7.44(4H, m). | 335(100%, [M+H]+) | — |
| 49 | 2.33(3H, s), 3.15(6H, s), 4.75(2H, d), 5.77(1H, br t), 7.13(1H, m), 7.25(1H, m), 7.39(1H, m), 7.46(4H, m), 7.59(1H, m), 8.42(1H, d). | 360(100%, [M+H]+) | oil |
| 50 | 2.30(3H, s), 3.16(6H, s), 4.73(2H, d), 5.82(1H, br t), 7.20(4H, m), 7.41(2H, m), 7.61(1H, m), 8.41(1H, d). | 378(100%, [M+H]+) | 107-109 |
| 51 | 3.44(3H, s), 3.80(2H, t), 4.56(2H, t), 4.82(2H, d), 6.79(1H, br s), 7.16(1H, m), 7.23(1H, m), 7.34(1H, s), 7.51(5H, m), 7.63(1H, m), 8.38(1H, d). | 377(100%, [M+H]+) | 97-99 |

Example 57

Kv1.5 Autopatch Electrophysiology

Cells stably transfected with cDNA for human Kv1.5 (in pEF6::VA-His-TOPO) were grown in Dulbecco's Modified Eagle media (DMEM) alpha supplemented with 10% Fetal Calf Serum (FCS), 20 µl/ml penicillin (5000 U/ml) streptomycin (5000 µg/ml), 10 µl/ml [100×] glutamine, and blasticidin (7.5 µg/ml).

The external bathing solution contained (in mM): 150 NaCl, 10 KCl, 100 Potassium Gluconate, 3 $MgCl_2$, 1 $CaCl_2$, 10 HEPES, pH 7.4. Patch pipettes were filled with an electrode solution of composition (in mM): 160 KCl, 0.5 $MgCl_2$, 10 HEPES, 1 EGTA, pH 7.4 with KOH.

Compounds were dissolved in DMSO (100%) and made up in the external bather at a concentration of 1 µM. All experiments were conducted at room temperature (22-24° C.).

A cell suspension (10 ml), with a density of 100,000 cells/ml, was aliquoted into a 15 ml centrifuge tube and transferred to an incubator (37° C., 5% $CO_2$) for approximately one hour before use. Following 60 min incubation, a tube was taken and centrifuged at 1000 rpm for 4 mins at room temperature. 9.5 ml supernatant was thene discarded, leaving a cell pellet at the bottom of the tube. The pellet was then resuspended using 100 µl of cold (4° C.), filtered (0.22 µm), 0.2% BSA/bather solution (0.02 g BSA/10 ml bather). The bottom of the tube was manually agitated gently until the solution became cloudy with cells. The 100 µl cell resuspension solution was then stored on the bench at 4° C. (using a Peltier-based temperature control device) until used.

A length of capillary glass (1B150F-4, WPI) was dipped into the cell suspension solution, such that ~3 cm column of fluid was taken up by capillary action. An Ag/AgCl wire was dropped into the non-dipped end of the capillary also. The outside of the solution-filled end of the capillary was then dried and the capillary was loaded into the AutoPatch™.

Borosilicate glass patch pipettes (from 1.5 mm OD, thin-walled filamented, GC150-TF capillary glass, Harvard) were pulled using a DMZ pipette puller (Zeitz Instruments), and were back-filled using the internal pipette solution, being careful that no bubbles remain at the tip or in the body of the pipette. Patch pipettes typically had resistances of 2.3-3.5 MΩ. Once filled, the pipette tip and a proportion of the shaft (~15 mm) were dipped into Sigmacote (Sigma). The recording pipette was then loaded into the AutoPatch™. Automated patch-clamping was initiated by the operator, but thereafter AutoPatch.exe continued the experiment providing that preset conditions and criteria were satisfied.

Whole cell patch-clamp recordings were made using the AutoPatch™ rig, which incorporated an EPC9 amplifier (HEKA, Germany) under control of Pulse software (v8.54, HEKA, Germany), a motion controller with 2 translators (Newport, UK), valve controller (VF1) and a c-level suction device all at room temperature (22-24° C.). This equipment was completely under the control of AutoPatch.exe and operator intervention was only made when there was a requirement to refill the drug reservoirs or to prevent the loss of a cell due to a technical error. Cells with an $R_{series}$ greater than 18MΩ were discounted from the experiment.

Qualification stages prior to perfusion and drug application ensured that the observed current met the criteria for the experiment. Only those cells with an $I_K$>500 μA were used for experiments. Cells were continuously perfused with external solution at a flow rate of 1.8-2 ml/minute. The perfusion chamber had a working volume of 80-85 μl and allowed for rapid exchange of drug solutions. Online analysis of the $hK_v1.5$ current during the application of compounds was performed by the AutoPatch™ software.

Electrophysiology voltage-step protocols and analysis of data was performed as follows. Data was sampled at 5 kHz, and filtered with a −3 dB bandwidth of 2.5 kHz. Cells were held at a voltage of −80 mV. Currents were evoked to a voltage step for 1000 ms in duration at 0 mV every 5 s. Currents were analysed using Pulsefit software (v8.54, HEKA, Germany), with the total charge measured during the whole of the voltage step. All other plots were produced using Igor Pro (WaveMetrics).

Kv1.5 channel electrophysiology data for the representative compounds described within are given in the table below.

| Example | Compound | % Inhibition @1 (μM) |
|---|---|---|
| 21 | 5-(4-Fluorophenyl)-N-(pyridin-2-ylmethyl)furo[2,3-d]pyrimidin-4-amine | 39.76 |
| 22 | 5-Phenyl-N-(pyridin-2'-ylmethyl)furo[2,3-d]pyrimidin-4-amine | 54.00 |
| 23 | 5-(4-Chlorophenyl)-N-(pyridin-2'-ylmethyl)furo[2,3-d]pyrimidin-4-amine | 83.80 |
| 24 | 5-(3,4-Dimethoxyphenyl)-N-(pyridin-2'-ylmethyl)furo[2,3-d]pyrimidin-4-amine | 15.81 |
| 25 | 5-(1,3-Benzodioxol-5'-yl)-N-(pyridin-2'-ylmethyl)furo[2,3-d]pyrimidin-4-amine | 65.17 |
| 26 | 6-Methyl-5-phenyl-N-(pyridin-2'-ylmethyl)furo[2,3-d]pyrimidin-4-amine | 83.00 |
| 42 | (2-Morpholin-4-yl-5-phenyl-furo[2,3-d]pyrimidin-4-yl)-puridin-2-ylmethyl-amine | 99.00 |
| 43 | 2-((2-Hydroxyethyl)-{5-Phenyl-4-[(pyridine-2-ylmethyl)-amino]-furo[2,3-d]pyrimidin-2-yl}-amino)-ethanol | 82.00 |
| 41 | $N^2$-(2-Methoxyethyl)-5-phenyl-$N^4$-pyridin-2-ylmethyl-furo[2,3-d]pyrimidine-2,4-diamine | 99.00 |
| 44 | 2-{5-Phenyl-4-[(pyridin-2-ylmethyl)-amino]furo[2,3-d]pyrimidin-2-ylamino}-propane-1,3-diol | 75.00 |
| 46 | $N^2,N^2$-Dimethyl-5-phenyl-$N^4$-pyridin-2-ylmethyl-furo[2,3-d]pyrimidine-2,4-diamine | 99.00 |
| 45 | 2-((2-Hydroxyethyl)-{5-(4-fluorophenyl)-4-[(pyridine-2-ylmethyl)-amino]-furo[2,3-d]pyrimidin-2-yl}-amino)-ethanol | 42.00 |
| 47 | $N^2,N^2$-Dimethyl-$N^4$-(6-methyl-pyridin-2-ylmethyl)-5-phenyl-furo[2,3-d]pyrimidine-2,4-diamine | 98.00 |
| 48 | $N^4$-Furan-2-ylmethyl-$N^2,N^2$-dimethyl-5-phenyl-furo[2,3-d]pyrimidine-2,4-diamine | 98.00 |
| 49 | 6,$N^2,N^2$-Trimethyl-5-phenyl-N4-pyridin-2-ylmethyl-furo[2,3-d]pyrimidine-2,4-diamine | 75.00 |
| 50 | 5-(4-Fluorophenyl)-6,$N^2,N^2$-trimethyl-$N^4$-pyridin-2-ylmethyl-furo[2,3-d]pyrimidine-2,4-diamine | 32.00 |
| 51 | [2-(2-Methoxyethoxy)-5-phenyl-furo[2,3-d]pyrimidin-4-yl]-pyridin-2ylmethylamine | 99.00 |

Abbreviations

| | |
|---|---|
| $KV_{(ur)}$ | Cardiac Ultrarapid Delayed Rectifier |
| CHO | Chinese Hamster Ovary Cells |
| DMEM | Dulbecco's Modified Eagle media |
| FCS | Fetal Calf Serum |
| EBSS | Earls Balanced Salt Solution |
| WCPC | Whole-Cell Patch-Clamp |

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Having now fully described this invention, it will be understood by hose of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

References

Herbert, "General principles of the structure of ion channels", Am. J. Med, 104, 87-98, 1998.

Armstrong & Hille, "Voltage-gated ion channels and electrical excitability", Neuron, 20, 371-380, 1998.

Gutman G A, Chandy K G, Adelman J P, Aiyar J, Bayliss D A, Clapham D E, Covarriubias M, Desir G V, Furuichi K, Ganetzky B, Garcia M L, Grissmer S, Jan L Y, Karschin A, Kim D, Kuperschmidt S, Kurachi Y, Lazdunski M, Lesage F, Lester H A, McKinnon D, Nichols C G, O'Kelly I, Robbins J, Robertson G A, Rudy B, Sanguinetti M, Seino S, Stuehmer W, Tamkun M M, Vandenberg C A, Wei A, Wulff H, Wymore R S International Union of Pharmacology. XLI. Compendium of voltage-gated ion channels: potassium channels. Pharmacol Rev. 2003 December; 55(4):583-6.

Shieh et al. "Potassium channels: molecular defects, diseases, and therapeutic opportunities", Pharmacol Rev, 52(4), 557-594, 2000.

Ford et al. "Potassium Channels: Gene Family, Therapeutic Relevance, High-Throughput Screening Technologies and Drug Discovery", Prog Drug Res, 58, 133-168, 2002.

Marban "Cardiac channelopalthies", Nature, 415, 213-218, 213-218, 2002.

Brendel and Peukert 'Blockers of the Kv1.5 Channel for the Treatment of Atrial Arrhythmias', Expert Opinion in Therapeutic Patents, 12 (11), 1589-1598 (2002).

Wang et al., "Sustained depolarization-induced outward current in human atrial myocytes. Evidence for a novel delayed rectifier $K^+$ current similar to Kv1.5 cloned channel currents", Circ Res, 73, 1061-1076, 1993.

Fedida et al., "Identity of a novel delayed rectifier current from human heart with a cloned K+ channel current", Circ Res, 73, 210-216, 1993.

Feng et al., "Antisense oligodeoxynucleotides directed against Kv1.5 mRNA specifically inhibit ultrarapid delayed rectifier $K^+$ current in cultured adult human atrial myocytes", Circ Res, 80, 572-579, 1997.

Amos et al., "Differences between outward currents of human atrial and subepicardial ventricular myocytes", J Physiol, 491, 31-50, 1996.

Li et al., "Evidence for two components of delayed rectifier $K^+$ current in human ventricular myocytes", Circ Res, 78, 689-696, 1996.

Nattel, 'Therapeutic implications of atrial fibrillation mechanisms: can mechanistic insights be used to improve AF management?' Cardiovascular Research, Volume 54, Issue 2, 347-360, 2002.

Courtemanche et al., "Ionic targets for drug therapy and atrial fibrillation-induced electrical remodeling: insights from a mathematical model", Cardiovasc Res, 42(2), 477-489, 1999.

Nattel et al., "Cardiac ultrarapid delayed rectifiers: a novel potassium current family of functional similarity and molecular diversity", Cell Physiol Biochem, 9(4-5), 217-226, 1999.

Knobloch K, Brendel J, Peukert S, Rosenstein B, Busch A E, Wirth K J. Electrophysiological and antiarrhythmic effects of the novel I(Kur) channel blockers, S9947 and S20951, on left vs. right pig atrium in vivo in comparison with the I(Kr) blockers dofetilide, azimilide, d,l-sotalol and ibutilide. Naunyn Schmiedebergs Arch Pharmacol. 2002 November; 366 (5):482-7.

Wirth K J, Paehler T, Rosenstein B, Knobloch K, Maier T, Frenzel J, Brendel J, Busch A E, Bleich M. Atrial effects of the novel K(+)-channel-blocker AVEO118 in anesthetized pigs. Cardiovasc Res. November 1; 60(2):298-306, 2003.

Colatsky et al., "Channel specificity in antiarrhythmic drug action. Mechanism of potassium channel block and its role in suppressing and aggravating cardiac arrhythmias", Circulation, 82(6), 2235-2242, 1990.

Feng et al., "Effects of class III antiarrhythmic drugs on transient outward and ultra-rapid delayed rectifier currents in human atrial myocytes", J Pharmacol Exp Ther, 281(1), 384-392, 1997.

Wang et al., "Effects of flecainide, quinidine, and 4-aminopyridine on transient outward and ultrarapid delayed rectifier currents in human atrial myocytes", J Pharmacol, 272 (1), 184-196, 1995.

Malayev et al., "Mechanism of clofilium block of the human Kv1.5 delayed rectifier potassium channel", Mol Pharmaco, 147(1), 198-205, 1995.

Godreau et al., "Mechanisms of action of antiarrhythmic agent bertosamil on hKv1.5 channels and outward potassium current in human atrial myocytes", J Pharmacol Exp Ther 300(2), 612-620, 2002.

Matsuda et al., "Inhibition by a novel anti-arrhythmic agent, NIP-142, of cloned human cardiac $K^+$ channel Kv1.5 current", Life Sci, 68, 2017-2024, 2001.

Bachmann et al., "Characterization of a novel Kv1.5 channel blocker in Xenopus oocytes, CHO cells, human and rat cardiomyocytes", Naunyn Schmiedebergs Arch Pharmacol, 364(5), 472-478, 2001.

Peukert S, Brendel J, Pirard B, Bruggemann A, Below P, Kleemann H W, Hemmerle H, Schmidt W. Identification, synthesis, and activity of novel blockers of the voltage-gated potassium channel Kv1.5. J Med. Chem. February 13; 46(4): 486-98, 2003.

Xu & Xu, "The expression of arrhythmic related genes on Xenopus oocytes for evaluation of class III antiarrhythmic drugs from ocean active material", Yi Chuan Xue Bao, 27(3), 195-201, 2000.

Antonov et al., Synthesis of heterocyclic compounds based on adducts of polyhaloalkanes with unsaturated systems. 6. Transformations of the trichloroethyl group in 2-methyl-3-(2,2,2-trichloroethyl)-4-(R-amino)furo[2,3-d]pyrimidines, their isomers and some of their precursors. Khimiya Geterotsiklicheskikh Soedinenii (1994), (4), 450-6.

Belenkii et al., Synthesis of heterocycles based on products of addition of polyhaloalkanes to unsaturated systems. 4. Synthesis of substituted furo[2,3-d]pyrimidines. Khimiya Geterotsiklicheskikh Soedinenii (1993), (1), 124-9.

What is claimed is:
1. A compound of formula

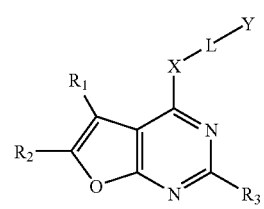

wherein
$R_1$ is aryl, heteroaryl, or cycloalkyl, each of which is optionally substituted;

$R_2$ is H, optionally substituted alkyl, nitro, $CO_2R_7$, $CONR_4R_5$ or halo;

$R_3$ is H, $NR_4R_5$, $NHC(O)R_8$, halo, trifluoromethyl, optionally substituted alkyl, cyano or alkoxy;

$R_4$ and $R_5$ may be the same or different, and may be H, optionally substituted alkyl, optionally substituted aryl, optionally substituted heteroaryl or optionally substituted cycloalkyl; or $R_4$ and $R_5$ may together form a saturated, unsaturated or partially saturated 4 to 7 member ring, wherein said ring may optionally comprise one or more further heteroatoms selected from N, O or S;

X is O, S or $NR_6$;

$R_6$ is H or optionally substituted alkyl;

$R_7$ is hydrogen, methyl or ethyl;

$R_8$ is methyl or ethyl; L is $(CH_2)_n$, where n is 1, 2 or 3; and

Y is aryl, a heterocyclic group, alkyl, alkenyl or cycloalkyl, each of which is optionally substituted;

or pharmaceutically acceptable salts thereof;

provided that the compound is not 4-diethylamino-5-phenylfuro [2,3-d]pyrimidine.

2. A compound according to claim 1 wherein $R_1$ is optionally substituted aryl or optionally substituted heteroaryl, $R_2$ is H or optionally substituted alkyl, $R_3$ is H, $NR_4R_5$, alkoxy or optionally substituted alkyl, X is O or $NR_6$, $R_6$ is H, n is 1 or 2 and Y is optionally substituted alkyl, optionally substituted cycloalkyl, optionally substituted aryl or optionally substituted heteroaryl.

3. A compound according to claim 2 wherein $R_1$ is optionally substituted aryl or optionally substituted heteroaryl, $R_2$ is H or methyl, $R_3$ is H, $NR_4R_5$, alkoxy or optionally substituted alkyl, X is $NR_6$, $R_6$ is H, n is 1 and Y is optionally substituted aryl or optionally substituted heteroaryl.

4. A compound according to claim 1 wherein Y is phenyl, furanyl, thienyl or pyridyl, each of which is optionally substituted.

5. A compound according to claim 1 wherein Y is optionally substituted phenyl, optionally substituted furan-2-yl or optionally substituted pyridin-2-yl.

6. A compound as claimed in claim 1 which is:
5-Phenyl-N-(pyridin-2-ylmethyl)furo[2,3-d]pyrimidin-4-amine,
5-(4-Chlorophenyl-N-(pyridin-2-ylmethyl)furo[2,3-d]pyrimidin-4-amine,
6-Methyl-5-phenyl-N-(pyridin-2-ylmethyl)furo[2,3-d]pyrimidin-4-amine,
(2-Morpholin-4-yl-5-phenyl-furo[2,3-d]pyrimidin-4-yl)-pyridin-2-ylmethyl-amine,
2-((2-Hydroxyethyl)-{5-Phenyl-4-[(pyridin-2-ylmethyl)-amino]-furo[-2,3-d]pyrimidin-2-yl }-amino)-ethanol,
2-((2-Hydroxyethyl)-{5-(4-fluorophenyl)-4[(pyridin-2-ylmethyl)-amino]-furo[2,3-d]pyrimidin-2-yl}-amino)-ethanol,
$N^2$-(2-Methoxyethyl)-5-phenyl-$N^4$-pyridin-2-ylmethyl-furo[2,3-d]pyrimidine-2,4-diamine,
2-{5-Phenyl-4-[(pyridin-2-ylmethyl)-amino] furo[2,3-d]pyrimidin-2-ylamino}-propane-1,3-diol,
$N^2,N^2$-Dimethyl-5-phenyl-$N^4$-pyridin-2-ylmethyl-furo[2,3-d]pyrimidine-2,4-diamine,
$N^2,N^2$-Dimethyl-$N^4$-(6-methyl-pyridin-2-ylmethyl)-5-phenyl-furo[2,3-d]pyrimidine-2,4-diamine, or
[2-(2-Methoxyethoxy)-5-phenyl-furo [2,3-d]pyrimidin-4-yl]-pyridin-2-ylmethylamine.

7. A process for preparing a compound according to claim 1 comprising:
(i) reacting a compound of formula II

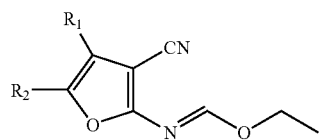

with a suitable nucleophile X-L-Y, optionally in the presence of a solvent and a base, and optionally at elevated temperature or with microwave irradiation; or (ii) reacting a compound of formula VI

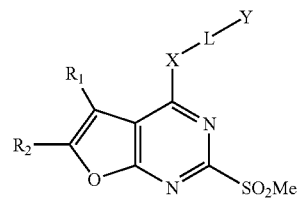

by displacement of the 2-methanesulphonyl substituent with a suitable nucleophilic species; or
(iii) reacting a compound of formula X

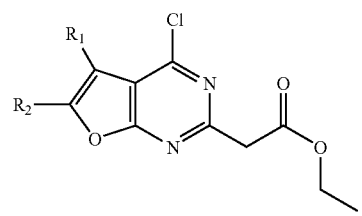

by displacement of the 4-chloro substituent with a suitable nucleophilic species.

8. A pharmaceutical composition comprising at least one compound according to claim 1 and one or more excipients, diluents, carriers, and mixtures thereof.

9. A pharmaceutical composition comprising a compound according to claim 6 and one or more excipients, diluents, carriers, and or mixtures thereof.

10. A method of treating arrhythmia, comprising administering to a subject an effective amount of at least one compound according to claim 1.

11. A method of treating arrhythmia, comprising administering to a subject an effective amount of at least one compound according to claim 6.

12. A compound according to claim 2, wherein Y is phenyl, furanyl, thienyl, or pyridyl.

13. A compound according to claim 3, wherein Y is phenyl, furanyl, thienyl, or pyridyl.

14. A compound according to claim 2, wherein Y is optionally substituted phenyl, optionally substituted furan-2-yl, or optionally substituted pyridin-2-yl.

15. A compound according to claim 2, wherein Y is optionally substituted phenyl, optionally substituted furan-2-yl, or optionally substituted pyridin-2-yl and $R_6$ is H.

16. A compound according to claim 3, wherein Y is optionally substituted phenyl, optionally substituted furan-2-yl, or optionally substituted pyridin-2-yl.

17. The process according to claim 7, wherein the compound prepared is selected from the group consisting of
5-Phenyl-N-(pyridin-2-ylmethyl)furo[2,3-d]pyrimidin-4-amine,
5-(4-Chlorophenyl-N-(pyridin-2-ylmethyl)furo[2,3-d]pyrimidin-4-amine,
6-Methyl-5-phenyl-N-(pyridin-2-ylmethyl)furo[2,3-d]pyrimidin-4-amine,
(2-Morpholin-4-yl-5-phenyl-furo[2,3-d]pyrimidin-4-yl)-pyridin-2-ylmethyl-amine,
2-((2-Hydroxyethyl)-{5-Phenyl-4-[(pyridin-2-ylmethyl)-amino]-furo[2,3-d]pyrimidin-2-yl }-amino)-ethanol, 2-((2-Hydroxyethyl)-{5-(4-fluorphenyl)-4[(pyridin-2-yl-methyl)-amino]-furo[2,3-d]pyrimidin-2-yl}-amino)-ethanol, $N^2$-(2-Methoxyethyl)-5-phenyl-$N^4$-pyridin-2-ylmethyl-furo[2,3-d]pyrimidine-2,4-diamine, 2-{5-Phenyl-4-[(pyridin-2-ylmethyl)-amino]furo[2,3-d]pyrimidin-2-ylamino}-propane-1,3-diol, $N^2,N^2$-Dimethyl-5-phenyl-$N^4$-pyridin-2-ylmethyl-furo[2,3-d]pyrimidine-2,4-diamine, $N^2,N^2$-Dimethyl-$N^4$-(6-methyl-pyridin-2-ylmethyl)-5-phenyl-furo[2,3-d]pyrimidine-2,4-diamine, and

[2-(2-Methoxyethoxy)-5-pheny-furo[2,3-d]pyrimidin-4-yl]-pyridin-2-ylmethylamine.

18. A compound according to claim 1 wherein $R_1$ is aryl, heteroaryl or cycloalkyl, each of which is unsubstituted.

19. A compound according to claim 1 wherein Y is heteroaryl, alkyl, alkenyl or cycloalkyl, each of which is unsubstituted.

20. A compound according to claim 1 wherein $R_6$ is H.

* * * * *